(12) United States Patent
Kamimura et al.

(10) Patent No.: US 6,925,143 B2
(45) Date of Patent: *Aug. 2, 2005

(54) X-RAY SENSOR SIGNAL PROCESSOR AND X-RAY COMPUTED TOMOGRAPHY SYSTEM USING THE SAME

(75) Inventors: Hiroshi Kamimura, Hitachi (JP); Shigeru Izumi, Tokyo (JP); Hiroshi Kitaguchi, Nakamachi (JP); Atsushi Yamagoshi, Hitachi (JP); Katsutoshi Satoh, Hitachi (JP); Noriyuki Sadaoka, Tokai (JP); Tarou Takagi, Hitachi (JP); Kouji Kuwabara, Hitachi (JP); Shouhei Numata, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/864,782

(22) Filed: Jun. 10, 2004

(65) Prior Publication Data

US 2004/0223582 A1 Nov. 11, 2004

Related U.S. Application Data

(63) Continuation of application No. 10/067,914, filed on Feb. 8, 2002, now Pat. No. 6,859,911, which is a continuation-in-part of application No. 09/517,590, filed on Mar. 3, 2000, now Pat. No. 6,366,636.

(30) Foreign Application Priority Data

Mar. 12, 1999 (JP) ........................................... 11-066023

(51) Int. Cl.[7] ................................................ A61B 6/03
(52) U.S. Cl. ............................. 378/19; 378/4; 378/901
(58) Field of Search ............................ 378/4, 8, 15, 19, 378/901

(56) References Cited

U.S. PATENT DOCUMENTS 4,748,649 A 5/1988 Griesmer et al.
5,043,582 A 8/1991 Cox et al.
5,578,825 A 11/1996 Cho et al.
5,661,293 A 8/1997 Ziegler et al.
5,949,842 A 9/1999 Schafer et al.
6,183,561 B1 2/2001 Belotserkovsky
6,366,636 B1 * 4/2002 Kamimura et al. ........... 378/19

FOREIGN PATENT DOCUMENTS

EP 0 026 108 A2 4/1981
JP 58-15847 1/1983
JP 2000-298106 10/2000

OTHER PUBLICATIONS

1996 IEEE Nuclear Science Symposium, Conference Record, vol. 2, pp. 816–820, Nov. 2–9, 1996, Anaheim, CA, USA.

Computer Image Processing, Version for Application and Practice, vol. 1, H. Tamura, Souken pubiication, pp. 18–29, 1990.

* cited by examiner

Primary Examiner—David V Bruce
(74) Attorney, Agent, or Firm—Antonelli, Terry, Stout & Kraus, LLP

(57) ABSTRACT

An X-ray CT apparatus having X-ray irradiator for irradiating an X-ray to an object to be inspected, an X-ray semiconductor sensor for detecting an X-ray passed through the object to be inspected, an X-ray sensor signal processing circuit for processing an output signal from the X-ray semiconductor sensor, and a CT control apparatus for reconstructing an image of the object to be inspected on the basis of the output signal of the X-ray semiconductor sensor processed by the X-ray sensor signal processing circuit. The X-ray sensor signal processing circuit includes a filter for removing a DC component from the output signal of the X-ray semiconductor sensor, and an integration circuit for integrating an output signal of the X-ray semiconductor sensor from which the DC component is removed by the filter.

6 Claims, 16 Drawing Sheets

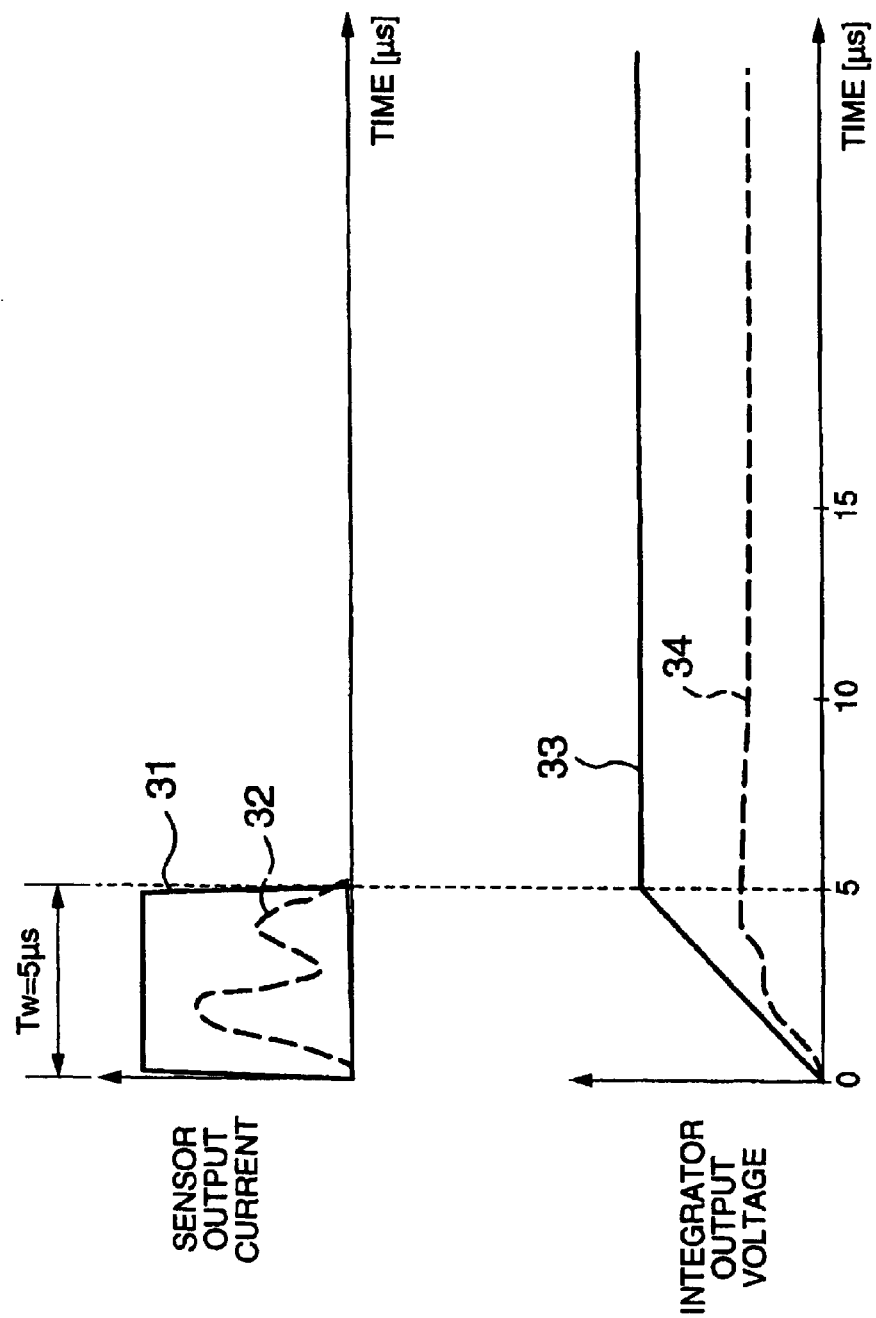

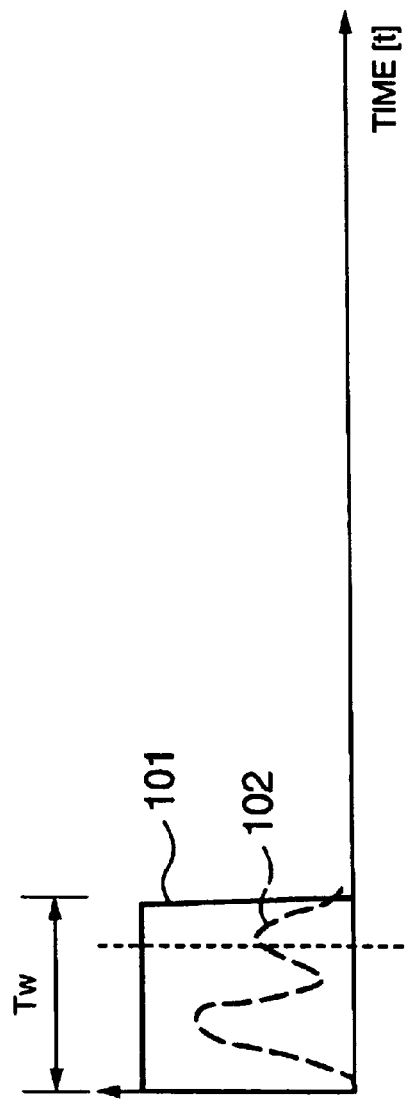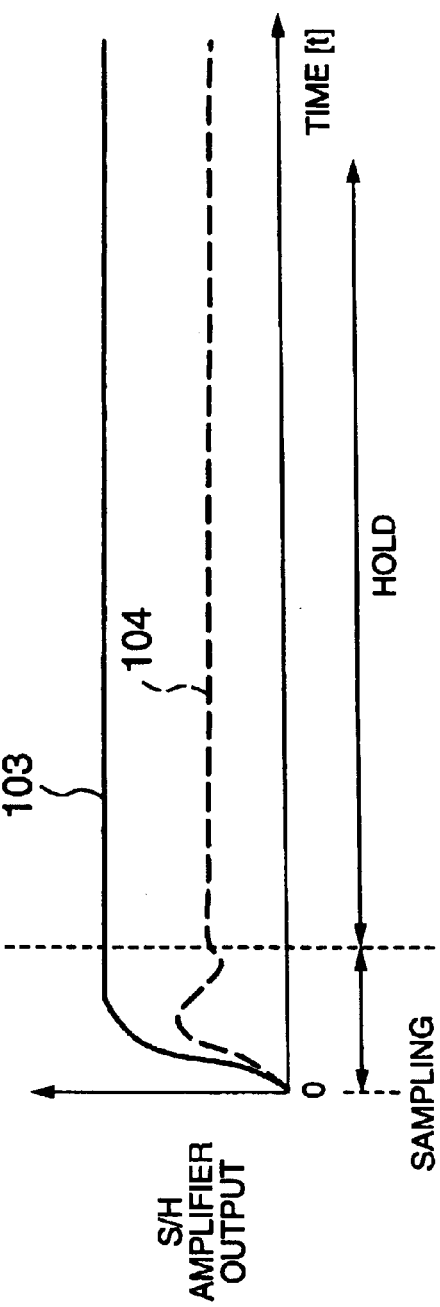
FIG.10A (PRIOR ART)
FIG.10B (PRIOR ART)

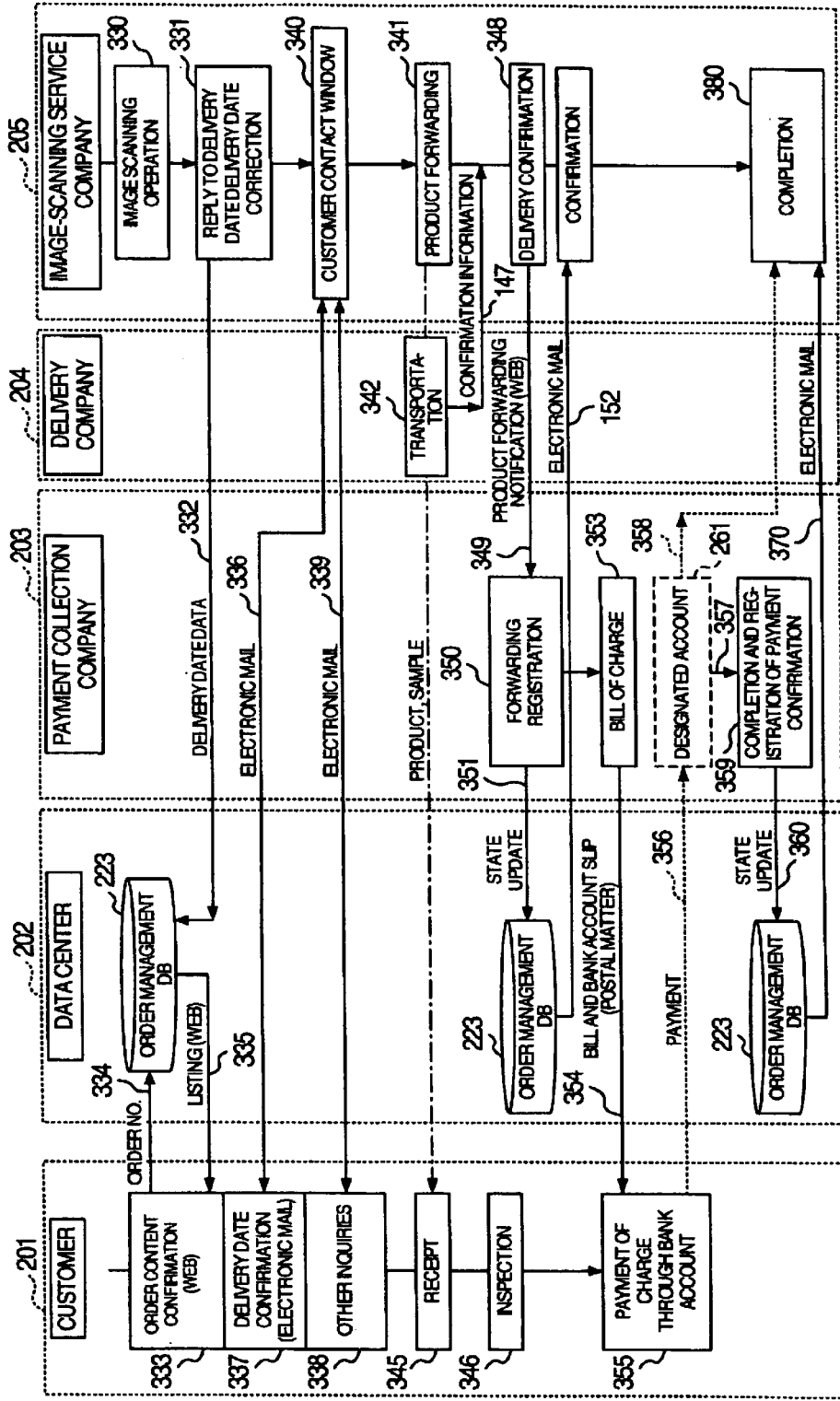

FIG.16

| | BASIC SERVICE | OPTIONAL SERVICE |
|---|---|---|
| 1. SPECIFIC SECTION PHOTOGRAPHY | DISPLAY BY 2D SECTIONS (2D BIT-MAP DATA + 2D IMAGE DATA) | MEASUREMENT OF DIMENSIONS |
| | | DISPLAY OF DENSITY DISTRIBUTION IN DESIGNATED LINE/REGION (PROFILE, GRAPH, COLOR DISTRIBUTION) |
| 2. STEREOSCOPIC IMAGE PHOTOGRAPHY | DISPLAY BY 3D STEREOSCOPIC IMAGE (3D BIT-MAP DATA + DISPLAY SOFTWARE) | VOLUME RENDERING |
| | | SLICING DISPLAY |
| | | DATA TRANSFORMATION |
| | | MEASUREMENT OF DIMENSIONS IN DESIGNATED POSITION |
| | | DISPLAY OF DENSITY DISTRIBUTION IN DESIGNATED LINE/REGION |
| 3. COMMON OPTION | — | ROENTGENOGRAM |
| | | ADDITION OF STANDARD SAMPLE DATA |
| | | SPECIAL MOUNTING (FROM 50 KG TO 100 KG) |
| | | EXPRESS SERVICE |

400

X-RAY SENSOR SIGNAL PROCESSOR AND X-RAY COMPUTED TOMOGRAPHY SYSTEM USING THE SAME

CROSS-REFERENCE TO RELATED APPLICATIONS

The present application is a continuation of U.S. application Ser. No. 10/067,914, filed Feb. 8, 2002, now U.S. Pat. No. 6,859,911, which is a continuation-in-part of U.S. patent application Ser. No. 09/517,590 filed on Mar. 3, 2000, now U.S. Pat. No. 6,366,636, under the title "X-RAY SENSOR SIGNAL PROCESSOR AND X-RAY COMPUTED TOMOGRAPHY SYSTEM USING THE SAME", the disclosures of which are hereby incorporated by reference.

BACKGROUND OF THE INVENTION

The present invention relates to an X-ray sensor signal processor for processing output signals of X-ray sensors for non-destructive inspection, and an X-ray computed tomography system (hereinafter referred to as "X-ray CT system") using the X-ray sensor signal processor. Particularly, it relates to an X-ray sensor signal processor in which a dark current generated in each of X-ray sensors can be removed and a value proportional to the average number of photons in X-rays can be obtained even in the case where a small number of incident photons are given, and an X-ray CT (computed tomography) system using the X-ray sensor signal processor.

Industrial X-ray CT systems using X-ray pulses with high energy (of 1 MeV or higher) have been developed in recent years for the purpose of non-destructively inspecting internal defects, or the like, of metallic parts or devices. Greater progress in research and development has been made for the purpose of inspecting a larger object with high resolution.

An X-ray CT system has been described in H. Miyai, et al. "A High Energy X-Ray Computed Tomography Using Silicon Semiconductor Detectors", 1996 Nuclear Science Symposium Conference Record, Vol. 2, pp. 816–820, Nov. 2–9, 1996, Anaheim, Calif., USA (1997) (hereinafter referred to as "first background art"). A signal processor for processing output signals of X-ray sensors shown in the first background art will be described below with reference to FIG. 9.

In the signal processor 1 shown in FIG. 9, semiconductor sensors (X-ray sensors) 21 to 2n are connected to first-stage circuits 90 to 9n respectively. Because a semiconductor sensor for an X-ray computed tomography is shaped like a strip of paper with a large size (for example, 3×40×0.4 mm) to detect a high-energy X-ray pulse efficiently, there is a possibility that a dark current with a high level of the order of tens of nA may be inevitably generated in the semiconductor sensor. In the first-stage circuit 90, a capacitor 114 is provided to AC-couple the semiconductor sensor 21 so that a voltage amplifier does not amplify a DC voltage caused by the dark current. When X-rays become incident onto the semiconductor sensor 21, an electric current flows through a capacitor 114 because electric charges are generated in the inside of the sensor. A voltage change generated on this occasion is amplified by two stages of voltage amplifiers 92 and 92', held by a sample/hold amplifier 94 and supplied to a posterior device.

FIG. 10A shows an output of the semiconductor sensor 21 in the first background art, and FIG. 10B shows an output of the sample/hold amplifier 94 in the first background art. An X-ray pulse is output with a pulse width Tw. Hence, when there is no object or when an object penetrated by the X-ray pulse is thin, the output of the X-ray sensor is provided as a rectangular-wave output 101 (solid line) proportional to the dose of the X-ray pulse as shown in FIG. 10A. Hence, the output of the sample/hold amplifier 94 is obtained as an output 103 proportional to the average number of photons per unit time except the first rising portion as shown in FIG. 10B.

On the contrary, when an X-ray pulses pass through a thick object, the number of incident photons is reduced by at least four digits compared with the case where no object is set, because the X-ray pulses are attenuated before the X-ray pulses become incident on the semiconductor sensor 21. The output 102 in FIG. 10A shows an example of the output of the semiconductor sensor 21 in the case where the object is so thick that a small number of incident photons are given. As shown in FIG. 10A, the output of the semiconductor sensor 21 is not kept constant but it has a waveform the output height of which is heightened only when photons are incident on the semiconductor sensor 21. In this case, the output of the sample-and-hole amplifier 94 is not kept constant, either, as represented by the output 104 in FIG. 10B. That is, the value held by the sample/hold amplifier 94 does not always express a voltage proportional to the average number of photons per unit time. As described above, the first background art has a problem that a voltage proportional to the average number of photons per unit time is not obtained when a small number of incident photons are given.

A technique for obtaining a voltage proportional to the average number of incident photons even in the case where a small number of incident photons are given has been described in JP-A-58-15847 (hereinafter referred to as "second background art"). In the second background art, there has been described a medical X-ray tomography system in which a voltage proportional to the average number of photons is obtained by a root mean square of fluctuation components obtained as a result of removal of a DC component from an output signal of an X-ray sensor by a capacitor. This technique is called "root mean square voltage technique" or "Campbell's technique".

Assume now the case where the second background art is applied to the first background art. Generally, the pulse width of an X-ray pulse used in the industrial X-ray CT system which is a subject of the first background art is set to be small (about 5 μs) compared with the medical X-ray tomography system which is a subject of the second background art. The pulse with such a small pulse width, however, cannot be removed by a capacitor. Hence, fluctuation components cannot be taken out exclusively by a capacitor even in the case where the second background art is applied to the industrial X-ray CT system which is a subject of the first background art. Because a voltage proportional to the average number of photons cannot be obtained accurately by the root mean square voltage technique if fluctuation components cannot be taken out exclusively, a voltage proportional to the average number of photons cannot be obtained accurately even in the case where the second background art is applied to the first background art as described above.

SUMMARY OF THE INVENTION

An object of the present invention is to provide an X-ray sensor signal processor in which a dark current generated in each X-ray sensor can be removed and a value proportional to the average number of photons in X-rays can be obtained even in the case where a small number of incident photons are given, and an X-ray CT system using the X-ray sensor signal processor.

The present invention is characterized by an X-ray sensor signal processor for processing an output signal of each X-ray sensor for detecting pulse-like X-rays emitted from an accelerator and passed through an object, wherein the processor comprises a filter for removing a DC component from the output signal of the X-ray sensor, and an integrator for integrating the output signal of the X-ray sensor after removal of the DC component by the filter.

According to the present invention, a dark current generated in the X-ray sensor can be removed because the capacitor for removing a DC component from the output signal of the X-ray sensor is provided, and a value proportional to the average number of photons in X-rays can be obtained by integration of the output signal of the X-ray sensor even in the case where a small number of incident photons are given because the integrator for integrating the output signal of the X-ray sensor after removal of the DC component is provided.

According to the present invention, a dark current generated in each of X-ray sensors can be removed and a value proportional to the average number of photons can be obtained even in the case where a small number of incident photons are given.

BRIEF DESCRIPTION OF THE DRAWINGS

FIGS. 3A and 3B show graphs showing the output current waveform of the semiconductor sensor 21 depicted in FIG. 1 and the output voltage waveform of the integrator depicted in FIG. 1.

FIGS. 10A and 10B show graphs showing the output current waveform of the semiconductor sensor 21 depicted in FIG. 9 and the output voltage waveform of the sample/hold amplifier 94 depicted in FIG. 9.

FIG. 15 is a diagram showing an example of an operation flow of image scanning business; and FIG. 16 is a diagram showing an example of a service menu for image scanning business.

DETAILED DESCRIPTION OF THE INVENTION

Embodiments of the present invention will be described below in detail by using the drawings.
(Embodiment 1)

Figure 1:
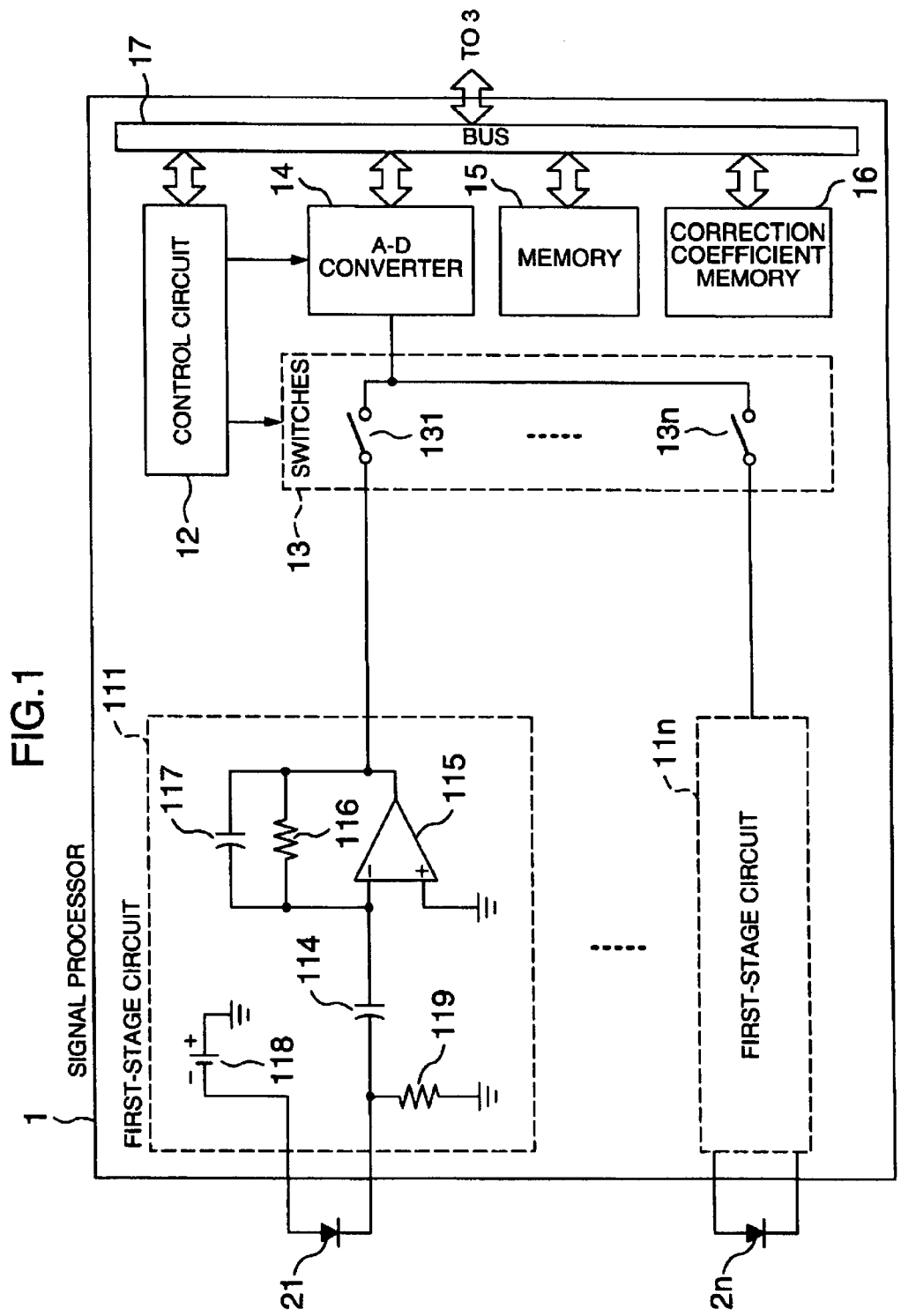
FIG. 1 shows a configuration diagram of a signal processor as a preferred embodiment of the present invention.

FIG. 1 shows an X-ray sensor signal processor which is a preferred embodiment of the present invention. FIG. 2 shows an X-ray CT system using the X-ray sensor signal processor depicted in FIG. 1.

Figures 2A, 2B:
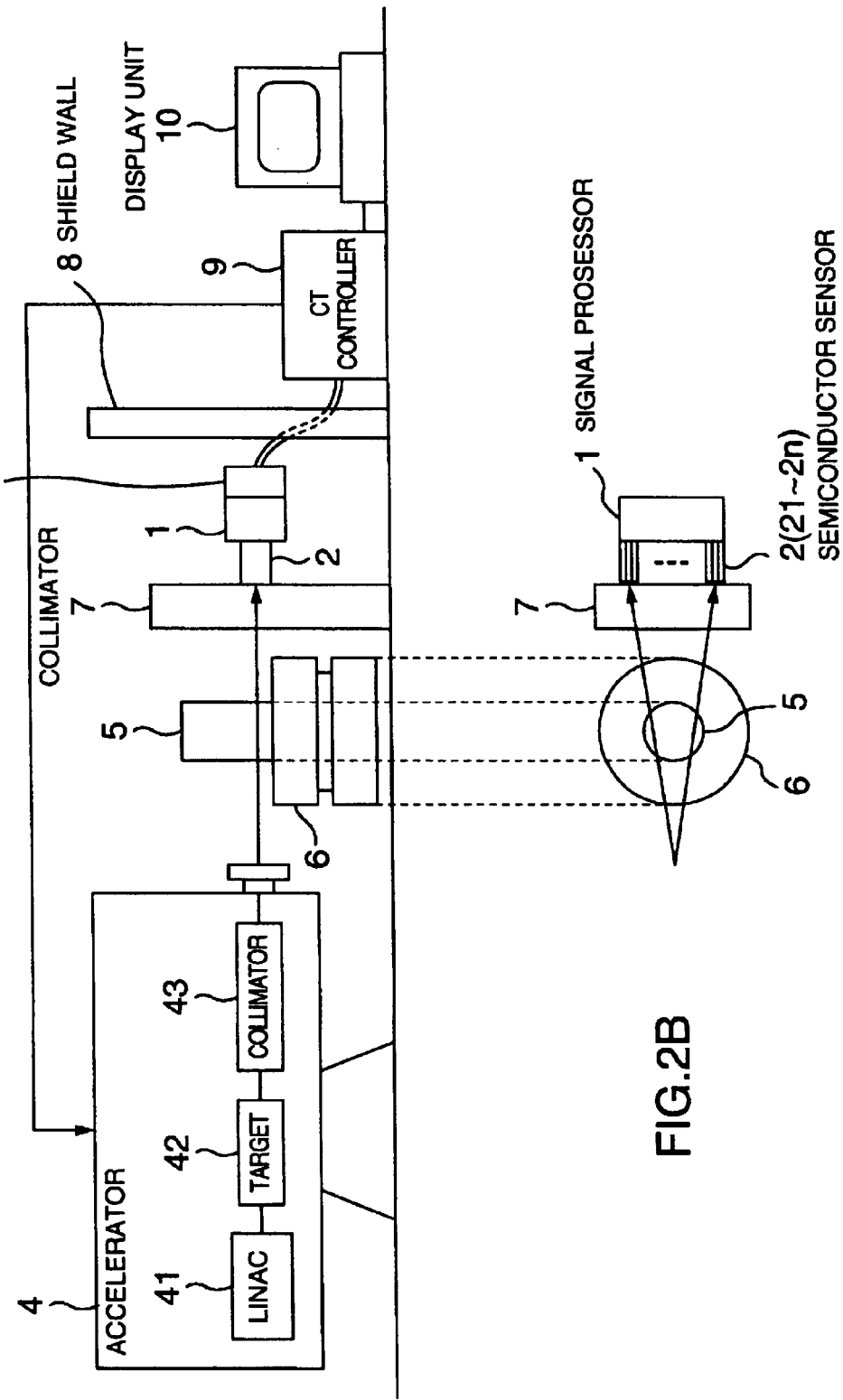
FIGS. 2A and 2B show configuration diagrams of an X-ray CT system as a preferred embodiment of the present invention.

Referring first to FIG. 2, non-destructive inspection by the X-ray CT system will be described. FIG. 2A is a side view of the X-ray CT system, and FIG. 2B is a partial top view of the X-ray CT system. In FIG. 2A, first, a CT controller 9 issues an X-ray pulse output command to an accelerator 4. At the same time when the CT controller 9 issues the X-ray pulse output command, the CT controller 9 issues an X-ray pulse output start signal to a signal processor (X-ray sensor signal processor) 1. Upon reception of the X-ray pulse output command, the accelerator 4 generates fan beam-like (radial) X-rays with high energy (not lower than 1 MeV) by irradiation of a target 42 with an ion beam acceleratively emitted from a linear accelerator 41 (hereinafter referred to as "LINAC"). The generated X-rays are emitted from the accelerator 4 through a collimator 43. Although the X-rays are emitted as a pulse with a short pulse width of 5 $\mu$s from the accelerator 4, both energy and pulse width of the ion beam irradiating the target 42 are controlled by the LINAC 41 so that both energy and pulse width of the X-rays are controlled.

The X-ray pulse emitted from the accelerator 4 irradiates an inspection object 5 disposed on a scanner 6 and passes through the object 5. A control signal not shown is given to the scanner 6 by the CT controller 9, so that the scanner 6 rotates and moves up and down in accordance with the control signal. By the rotation and up-down movement of the scanner 6, any portion of the object 5 is irradiated with X-ray pulses from various directions by a plurality of times. The X-ray pulses passed through the object 5 are incident on an array of semiconductor sensors (X-ray sensors) 21 to 2n via the collimator 7. When the X-rays are incident on a depletion layer of a p-n junction in any one of the semiconductor sensors 21 to 2n, a large number of electron-hole pairs are generated so that an electric current flows in the semiconductor sensor. The signal processor 1 issues sensor output data corresponding to the electric currents generated in the semiconductor sensors 21 to 2n. The operation of the signal processor 1 will be described later.

A data transmitter-receiver circuit 3 receives the sensor output data from the signal processor 1 and transmits the sensor output data to the CT controller 9. Incidentally, data transfer between the data transmitter-receiver circuit 3 and the CT controller 9 is performed through a cable passing through a shield wall 8 because there is the shield wall 8 between the data transmitter-receiver circuit 3 and the CT controller 9. Both data transfer between the accelerator 4 and the CT controller 9 and data transfer between the scanner 6 and the CT controller 9 are performed through the cable in the same manner as described above. The CT controller 9 reconstructs a perspective image of a section of the object 5 by using the sensor output data given to the CT controller 9 and makes a display unit 10 display the perspective image.

In the aforementioned manner, a perspective image of a section of the object 5 is obtained.

Referring next to FIG. 1, the signal processor 1 will be described. In FIG. 1, the semiconductor sensors 21 to 2n are connected to first-stage circuits 111 to 11n respectively.

Incidentally, only one first-stage circuit 111 will be described hereafter because each of the first-stage circuits 112 (not shown) to 11n has the same configuration as that of the first-stage circuit 111.

In the first-stage circuit 111, a bias supply 118 is connected to one end of the semiconductor sensor 21 in a direction of applying a reverse bias to the semiconductor sensor 21, and a resistor 119 is connected to the other end of the semiconductor sensor 21. Incidentally, the other end of the resistor 119 is connected to the ground. Further, a capacitor 114 is connected to a junction between the semiconductor sensor 21 and the resistor 119. The other end of the capacitor 114 is connected to an inverting input of an operational amplifier 115. A resistor 116 and a capacitor 117 are connected in parallel to the operational amplifier 115. The operational amplifier 115, the resistor 116 and the capacitor 117 form an integrator. Hereinafter, the operational amplifier 115, the resistor 116 and the capacitor 117 will be collectively called "integrator". The first-stage circuit 111 is configured as described above.

As described above in the background art, a dark current of the order of tens of nA is generated in the semiconductor sensor 21. This dark current is, however, a DC component. Hence, the dark current does not flow into the integrator through the capacitor 114 but flows into the resistor 119. In the first-stage circuit 111, the dark current is removed in this manner.

When an X-ray pulse is detected by the semiconductor sensor 21, the frequency band of the output current of the semiconductor sensor 21 is not lower than the order of tens of kHz because the pulse width of the X-ray pulse is 5 $\mu$s. Hence, the output current flows into the integrator through the capacitor 114. Because the inverting input of the operational amplifier 115 forms an imaginary short circuit, the output current little flows into the resistor 116 but flows into the capacitor 117. Hence, electric charges are stored in the capacitor 117. When the X-ray pulse detection in the semiconductor sensor 21 is completed, the electric charges stored in the capacitor 117 are discharged (attenuated) in accordance with the time constant determined on the basis of the combination of the resistor 116 and the capacitor 117 because the output current from the semiconductor sensor 21 is merely constituted by the dark current as a DC component. Incidentally, a method for determining the resistance R of the resistor 116 and the capacitance C of the capacitor 117, that is, a method for determining the time constant will be described later.

FIG. 3A shows the output current waveform of the semiconductor sensor 21, and FIG. 3B shows the output voltage waveform of the integrator constituted by the combination of the operational amplifier 115, the resistor 116 and the capacitor 117. In FIG. 3A, an output waveform 31 (solid line) shows the output waveform of the semiconductor sensor 21 in the case where an X-ray pulse not passed through the object 5 is incident on the semiconductor sensor 21, and the other output waveform 32 shows the output waveform of the semiconductor sensor 21 in the case where the number of incident photons in the X-ray pulse incident on the semiconductor sensor 21 is reduced to a one-digit number because the X-ray pulse passes through a thick portion of the object 5. As described above in the background art, the output waveform of the semiconductor sensor 21 is shaped to be a rectangular in proportion to the dose of the X-ray pulse in the case where the X-ray pulse does not pass through the object 5 whereas the output waveform of the semiconductor sensor 21 is shaped so as to be heightened only when photons are incident on the semiconductor sensor 21 in the case where the X-ray pulse passes through a thick portion of the object 5.

As shown in FIG. 3B, in the case where the X-ray pulse does not pass through the object 5, the integrator output corresponding to the sensor output increases substantially linearly during the current output from the semiconductor sensor 21 and then electric discharge occurs gradually (output 33: solid line). On the contrary, in the case where the X-ray pulse passes through a thick portion of the object 5, the output of the semiconductor sensor 21 is integrated so that a voltage proportional to the number of incident photons is obtained. That is, in the case where the X-ray pulse passes through a thick portion of the object 5, a voltage proportional to the number of incident photons can be obtained in this embodiment because an integrated value is calculated by use of the integrator even if the output waveform of the semiconductor sensor 21 changes with the passage of time.

In this manner, according to the first-stage circuit 111 in this embodiment, a voltage proportional to the average number of photons in X-rays can be obtained accurately, whether the X-ray pulse passes through the object 5 or not. Furthermore, no sample/hold amplifier needs to be provided in this embodiment because the integrator in this embodiment serves also as an sample/hold amplifier shown in the first background art. In addition, in this embodiment, the bias state of the semiconductor sensor 21 or the capacitor 114 returns to a steady state immediately after the completion of the X-ray pulse irradiation because all electric charges generated by the X-ray pulse are stored in the capacitor 117. Hence, no reset switch needs to be provided. In this manner, according to the first-stage circuit 111 in this embodiment, hardware configuration can be simplified. Incidentally, as described above, each of the first-stage circuits 112 to 11n has the same configuration as that of the first-stage circuit 111.

Output ends of the first-stage circuits 111 to 11n (output ends of the integrators) are connected to switches 131 to 13n, respectively, in a multiplexer 13. A control circuit 12 issues a "close" command to the switch 131 after 10 $\mu$s from the start of X-ray pulse irradiation. Incidentally, an X-ray pulse emission start signal output from the CT controller 9 is supplied to the control circuit 12 through the data transmitter-receiver circuit 3 and a bus 17. Hence, if irradiation starts when the X-ray pulse emission start signal is supplied to the control circuit 12, the control circuit 12 issues the "close" command after 10 $\mu$s from the start of irradiation. Upon reception of the "close" command, the switch 131 is closed so that the output signal of the first-stage circuit 111 is supplied to the A-D converter 14. The control circuit 12 issues "open" and "close" commands so that the switches 131 to 13n are closed successively at intervals of 5 $\mu$s.

Then, the control circuit 12 issues an A-D conversion command to the A-D converter 14. Upon reception of the A-D conversion command, the A-D converter 14 converts the output signal of the first-stage circuit 111 into a digital output signal. The output signal obtained by the A-D conversion is stored in a memory 15 through the bus 17 by the control circuit 12. Incidentally, the memory 15 has storage regions which are provided in advance correspondingly to the semiconductor sensors 21 to 2n (first-stage circuits 111 to 11n) respectively. Hence, the aforementioned output signal is stored in a storage region corresponding to the semiconductor sensor 21.

Then, the control circuit 12 issues an "open" command to the switch 131 after 15 $\mu$s from the start of X-ray pulse irradiation, that is, after 5 $\mu$s from the issue of the "close"

command to the switch 131. At the same time, the control circuit 12 issues a "close" command to the switch 132. Upon reception of the "open" command, the switch 131 is opened. Upon reception of the "close" command, the switch 132 is closed. As a result of the closing of the switch 132, the output signal of the first-stage circuit 112 is supplied to the A-D converter 14. Then, the control circuit 12 issues an A-D conversion command to the A-D converter 14, so that the A-D converter 14 converts the output signal of the first-stage circuit 112 into a digital output signal. The output signal obtained by the A-D conversion is stored in a storage region of the memory 15 corresponding to the semiconductor sensor 22 through the bus 17 by the control circuit 12.

The same processing as applied to the first-stage circuits 111 and 112 is hereafter applied to the other first-stage circuits 113 to 11$n$.

On this occasion, the output signal in each of the first-stage circuits 111 to 11$n$ is an output signal at a point of time when a predetermined time is passed after the completion of X-ray pulse irradiation. Hence, the level of the output signal at this point of time is smaller than that just after the completion of X-ray pulse irradiation. That is, the level of the output voltage of the integrator in each of the first-stage circuits 111 to 11$n$ is reduced with the passage of time because the output voltage is attenuated on the basis of the time constant determined by the product of the resistance R of the resistor 116 and the capacitance C of the capacitor 117 as described above. In this embodiment, therefore, the output signal stored in the memory 15 is corrected so that an output signal just after the completion of X-ray pulse irradiation is obtained.

The output signal level V0 just after the completion of X-ray pulse irradiation is expressed by the following expression 1.

$$V0=V(t)\times\exp(t/\tau) \quad \text{(Expression 1)}$$

In the expression 1, t is the time from the completion of X-ray pulse irradiation, V(t) is the output signal level at time t, and $\tau$ is the time constant. In the case of the first-stage circuit 111, t is 5 $\mu$s because the time required for measurement of the output signal just after the completion of X-ray pulse irradiation is 5 $\mu$s. Incidentally, t for each of the first-stage circuits 111 to 11$n$ can be obtained in advance so that t=10 $\mu$s for the first-stage circuit 112, t=15 $\mu$s for the first-stage circuit 113, and so on, because the switches 131 to 13$n$ are closed successively at intervals of 5 $\mu$s as described above. Also the time constant $\tau$ can be obtained in advance on the basis of the product of the resistance R of the resistor 116 and the capacitance C of the capacitor 117. Hence, the output signal level V0 at the point of time just after the completion of X-ray pulse irradiation can be obtained on the basis of the expression 1.

In this embodiment, values are substituted for t and $\tau$ in exp(t/$\tau$) and exp(t/$\tau$) is stored, as a correction coefficient for corresponding one of the semiconductor sensors 21 to 2$n$ (first-stage circuits 111 to 11$n$), in a correction coefficient memory 16 in advance. Each of the output signal levels stored in storage regions of the memory 15 corresponding to the semiconductor sensors 21 to 2$n$ is corrected to the output signal level V0 at the point of time just after the completion of X-ray pulse irradiation by the control circuit 12 with use of a corresponding correction coefficient stored in the correction coefficient memory 16 in advance (that is, the output signal level is multiplied by a corresponding correction coefficient). The corrected output signal levels V0 are overwritten in storage regions of the memory 15 corresponding to the semiconductor sensors 21 to 2$n$ respectively. The output signal levels stored in the memory 15 are supplied, as sensor output data, to the data transmitter-receiver circuit 3 in response to the request of the CT controller 9.

The aforementioned processing is repeated whenever X-ray pulse irradiation is performed once. On this occasion, the output signals of the first-stage circuits 111 to 11$n$, that is, the output signals of the integrators must be held until the output signal of the first-stage circuit 11$n$ is converted into a digital signal by the A-D converter 14 but the levels of the output signals must become zero until the next X-ray pulse irradiation. It is, therefore, necessary that the time constant for each integrator determined by the combination of the resistor 116 and the capacitor 117 is set to an appropriate value.

A method for determining the resistance R of the resistor 116 and the capacitance C of the capacitor 117 in this embodiment will be described below. The following five matters must be considered when the resistance R of the resistor 116 and the capacitance C of the capacitor 117 are to be determined.

(1) Qmax [C]: maximum quantity of electric charges generated by each of the semiconductor sensors 21 to 2$n$;
(2) m [digits]: dynamic range necessary for measurement;
(3) Vfs [V]: input range (maximum input voltage) of the A-D converter 14;
(4) n [bits]: required resolution; and
(5) Tp [s]: cycle period of X-ray pulse.

In the case where the X-ray pulse does not pass through the object 5, the output of each of the semiconductor sensors 21 to 2$n$ reaches Qmax but the output voltage of corresponding one of the first-stage circuits 111 to 11$n$ must not exceed the input range Vfs of the A-D converter 14. Further, the output signal level of the corresponding one of the first-stage circuits 111 to 11$n$ must be attenuated to a value not higher than a voltage corresponding to the required resolution n in the time Tp (set to 5 ms in this embodiment) which is required before incidence of the next X-ray pulse.

The maximum output Vmax of each of the integrators is determined by the following expression 2.

$$V\text{max}=Q\text{max}/C \quad \text{(Expression 2)}$$

The relation Vmax$\leq$Vfs must be established because Vmax over the input range Vfs of the A-D converter 14 cannot be measured.

Hence, the following expression 3 is deduced from the expression 2.

$$C\geq Q\text{max}/Vfs \quad \text{(Expression 3)}$$

Further, because the A-D converter 14 requires sufficient resolution to measure a smaller value by m digits than Vmax, the following expression 4 must be established if the attenuation of the signal before completion of the A-D conversion by the A-D converter 14 is neglected for the sake of simplification.

$$V\text{max}\times 10^{-m}=Q\text{max}/C\times 10^{-m}>Vfs/2^n \quad \text{(Expression 4)}$$

On the other hand, the output of the integrator is attenuated on the basis of the time constant $\tau=R\times C$. Hence, the maximum output Vmax of the integrator is attenuated as expressed by the following expression 5 at time t.

$$V(t)=V\text{max}\times\exp(-t/\tau) \quad \text{(Expression 5)}$$

When measurement resolution of n [bits] is required, V(t) must be attenuated to be not higher than a voltage corresponding to the required resolution in the time Tp before incidence of the next X-ray pulse. Hence, the following expression 6 must be satisfied.

$$V(Tp)=V\mathrm{max}\times\exp(-Tp/\tau)\leq V\mathrm{max}/2^n \quad \text{(Expression 6)}$$

Accordingly, the time constant τ is given by the following expression 7.

$$\tau=R\times C\leq Tp/(n+1n2) \quad \text{(Expression 7)}$$

Further, from the relations among the expressions 3, 4 and 7, C is given by the following expression 8.

$$Q\mathrm{max}/Vfs\leq C\leq \min\{(Q\mathrm{max}\times10^{-m}\times2^n)/Vfs, Tp/(R(n+1n2))\} \quad \text{(Expression 8)}$$

Incidentally, the function "min( )" means selection of smaller one of factors. In this embodiment, the cycle time Tp of X-ray pulses can be kept constant by trigger control of the accelerator because this embodiment is applied to an industrial X-ray CT system. When accuracy of 14-bit resolution (n=14) is required in use of a general A-D converter of 10 [V] full range (Vfs=10 [V]), it is apparent from the expression 8 that C needs to be set in a range of 15 [pF]<C<34 [pF] if the resistance R is 10 [MΩ] because the maximum quantity of electric charges in the sensor in this embodiment is about 150 [pC] (Qmax=150 [pC]). If the resistance R of the resistor 116 is determined in the aforementioned manner, an appropriate value of the capacitance C of the capacitor 117 can be obtained by calculation using the expression 8.

Figure 4:
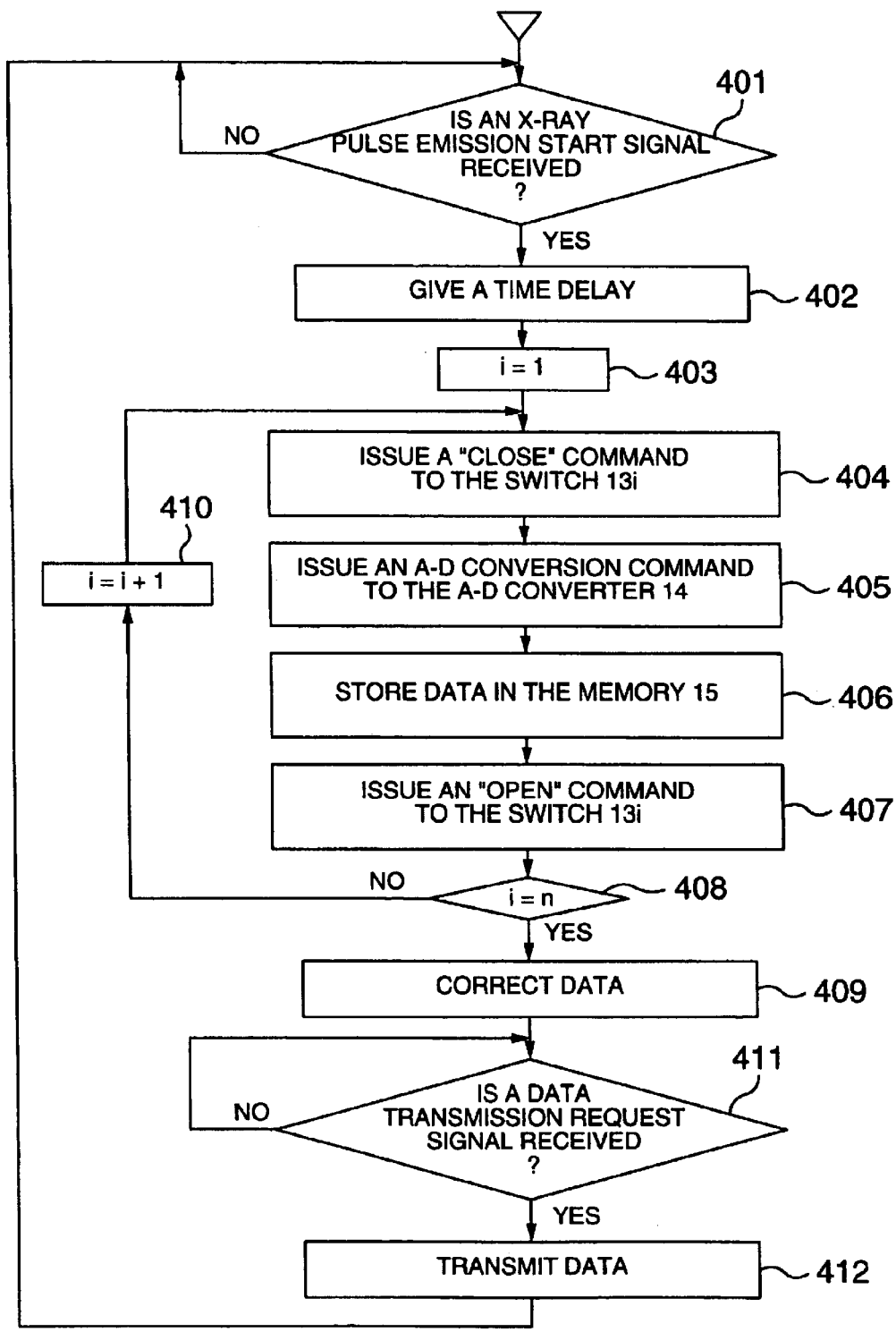
FIG. 4 shows a flow chart showing the operation of the control circuit 12 depicted in FIG. 1.

FIG. 4 is a flow chart showing the operation of the control circuit 12. The control circuit 12 judges whether an X-ray pulse emission start signal is received from the data transmitter-receiver circuit 3 or not. The situation of the routine goes to step 402 when the X-ray pulse emission start signal is received whereas the judgment in step 401 is repeated when the X-ray pulse emission start signal is not received (step 401). When the X-ray pulse emission start signal is supplied to the control circuit 12, processing of the output signals of the semiconductor sensors 21 to 2n starts after a predetermined delay time (10 μs in this embodiment) is passed (step 402).

First, semiconductor sensor number i to be subjected to output signal processing is set to be 1 (step 403). Then, a "close" command is issued to a corresponding switch 13i of the multiplexer 13 (step 404). An A-D conversion command is issued to the A-D converter 14 (step 405). When the A-D conversion by the A-D converter 14 is completed, the data is stored in the memory 15 (step 406) and an "open" command is issued to the switch 13i of the multiplexer 13 (step 407). Then, a judgment is made as to whether i is equal to n or not (whether measurement on all the semiconductor sensors 21 to 2n is performed or not) (step 408). If i is equal to n, the situation of the routine goes to step 409. If i is not equal to n, the situation of the routine goes to step 410. In the step 410, the calculation i=i+1 is made and then the situation of the routine goes back to the step 404.

After the output signals of the semiconductor sensors 21 to 2n are A-D converted and stored in the memory 15 in the aforementioned manner, the output signals stored in the memory 15 are corrected on the basis of correction coefficients stored in the correction coefficient memory 16 and are overwritten in the memory 15 again (step 409). Then, a judgment is made as to whether a data transmission request signal is received from the data transmitter-receiver circuit 3 or not (step 411). At a point of time when there is the judgment that the data transmission request signal is received, the corrected output signals stored in the memory 15 are transmitted to the data transmitter-receiver circuit 3 (step 412). When data transmission is completed, the situation of the routine goes back to the step 401. The output signals of the semiconductor sensors 21 to 2n are processed by the aforementioned operation of the control circuit 12.

Although this embodiment has shown the case where the data correction step 409 is provided between the steps 408 and 411, the invention may be applied also to the case where the data correction step is provided between the steps 406 and 407. That is, correction may be made whenever the output signal of one semiconductor sensor is processed. The outputs of the integrators are, however, attenuated while data correction is made. Accordingly, higher accurate measurement can be made when correction is made at once after all the output signals of the semiconductor sensors 21 to 2n are stored in the memory as described above in this embodiment.

As described above, according to this embodiment, a dark current generated in each of the semiconductor sensors 21 to 2n can be removed because the capacitor 114 is provided for removing a DC component from the output current of each of the semiconductor sensors 21 to 2n. Furthermore, a value proportional to the average number of photons in X-rays can be obtained accurately by integration by a corresponding integrator even in the case where a small number of incident photons are given because the integrator constituted by the combination of the operational amplifier 115, the resistor 116 and the capacitor 117 is provided.

Although this embodiment has shown the case where the correction coefficient memory 16 is provided newly, there is no fear that the hardware amount is increased by addition of the correction coefficient memory 16 because the memory 15 and the correction coefficient memory 16 can be set in one chip sufficiently. Hence, in comparison between the hardware amount in this embodiment and that in the first background art, the first background art requires three IC's per semiconductor sensor for forming two operational amplifiers and one sample/hold amplifier whereas this embodiment requires one IC per semiconductor sensor for forming one operational amplifier. In this embodiment, the number of IC's can be reduced to one thirds. If the fact that a large number of semiconductor sensors are provided is considered, the hardware amount of the signal processor in this embodiment can be reduced by half as a whole compared with the first background art. According to this embodiment, the hardware amount of the signal processor can be reduced in the aforementioned manner, so that the production cost can be reduced.

Figure 8:
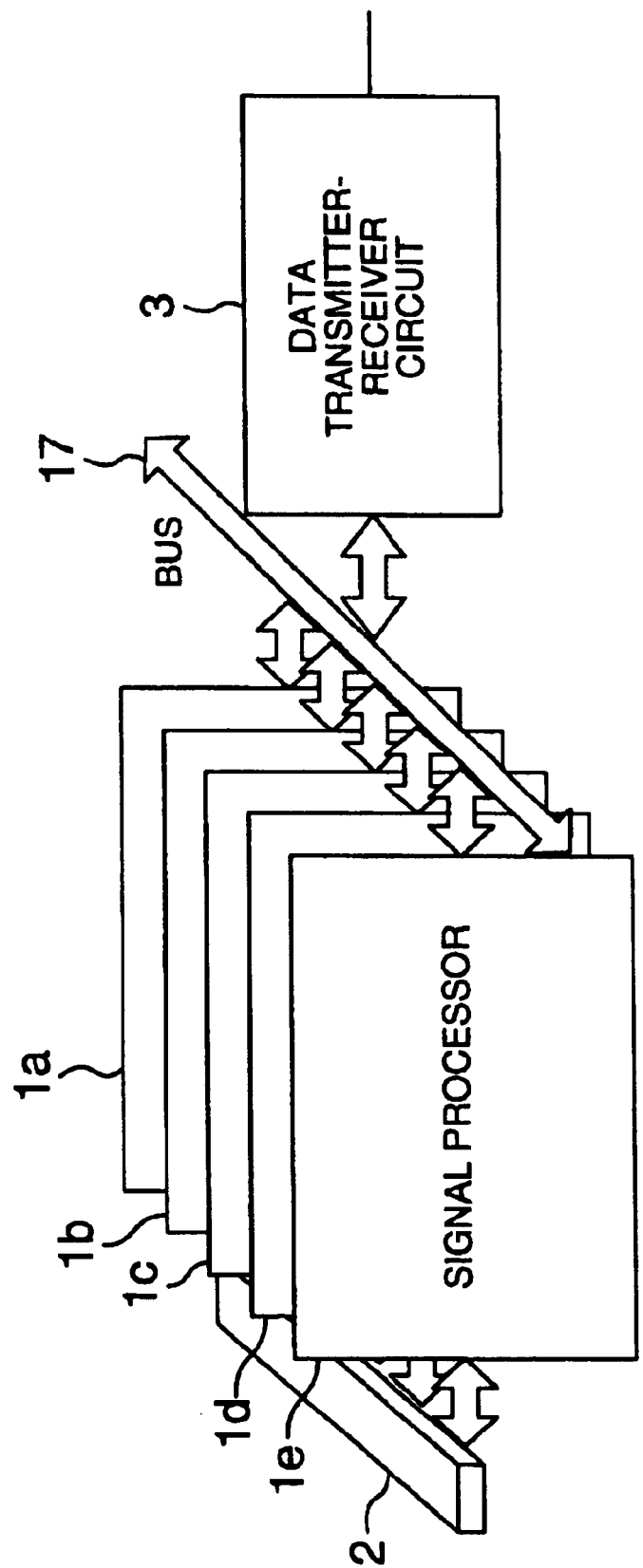
FIG. 8 shows a configuration diagram in the case where five signal processors 1a to 1e are used in the embodiment of FIG. 1.
Figure 9:
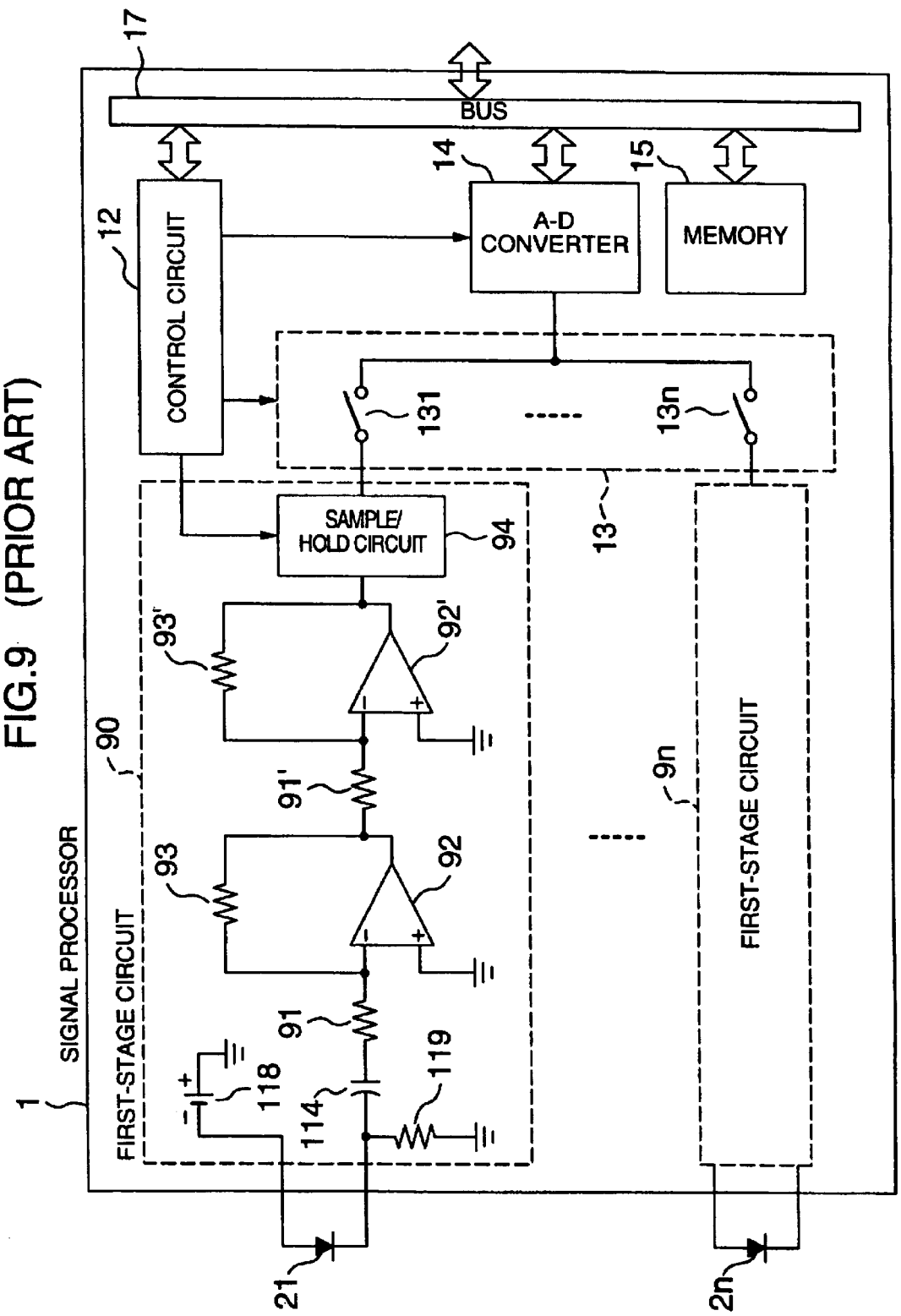
FIG. 9 shows a configuration diagram of a signal processor in the first background art.

Incidentally, the signal processor 1 described above in this embodiment may be separated into a plurality of circuit boards so that the throughput time can be shortened by parallel processing in each of the circuit boards. FIG. 8 shows a configuration in the case where five signal processors 1a to 1e are used. Incidentally, the signal processors 1a to 1e are formed on separate circuit boards, respectively. Further, as shown in FIG. 8, the bus 17 is provided in common with all the signal processors 1a to 1e. In this case, the signal processors 1a to 1e can operate in parallel with one another except for data transmission to the data transmitter-receiver circuit 3. Hence, signal processing can be performed rapidly, that is, high accurate measurement can be made before the output signals of the first-stage circuits are attenuated. Incidentally, because data transmission to the data transmitter-receiver circuit 3 is made in accordance with the request of the data transmitter-receiver circuit 3, there is no risk of crosstalk. Further, the number of circuit boards can be increased arbitrarily if addresses are allocated to the signal processors in advance.

Although the aforementioned embodiment has shown the case where the output signals of the first-stage circuits 111 to 11*n* are processed successively at intervals of 5 µs, the processing interval may be shortened if the time required for the A-D conversion in the A-D converter 14 can be shortened. Further, the control circuit 12 may be produced in combination with a digital circuit or may use a one-chip microcomputer. Although circuits for supplying power to the respective electronic circuits are not shown, it is a matter of course that such power supply circuits are connected to the respective electronic circuits in the first-stage circuits 111 to 11*n*.

(Embodiment 2)

Figure 5:
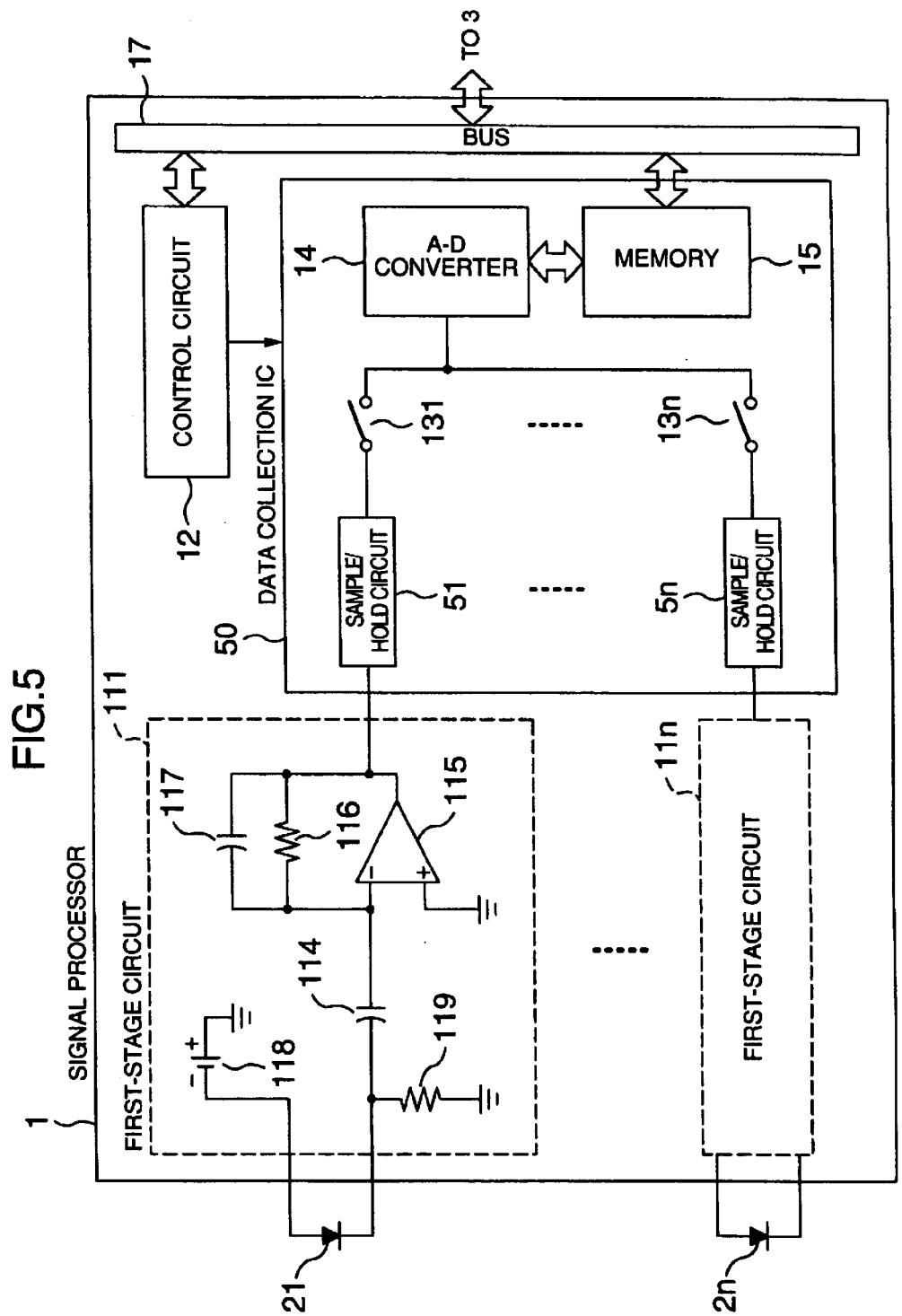
FIG. 5 shows a configuration diagram of a signal processor as another embodiment of the present invention.

Referring to FIG. 5, a signal processor as another embodiment of the present invention will be described below. This embodiment is different from the embodiment 1 in that a data collection IC in which sample/hold circuits and a multiplexer are incorporated in an A-D converter is used in this embodiment. The point of difference from the embodiment 1 will be described below.

As shown in FIG. 5, the data collection IC 50 has sample/hold circuits 51 to 5*n*, multiplexing switches 131 to 13*n*, an A-D converter 14, and a memory 15. The output signals of the first-stage circuits 111 to 11*n* are supplied to the sample/hold circuits 51 to 5*n* in the data collection IC and held immediately by the sample/hold circuits 51 to 5*n* respectively. The held output signals are supplied to the A-D converter through the switches 131 to 13*n* respectively. After A-D conversion, the output signals are stored in the memory 15. Incidentally, the same method as in the embodiment 1 is used as a method for controlling the switches 131 to 13*n*, the A-D converter 14 and the memory 15.

Also in this embodiment, like the embodiment 1, a dark current generated in each of the semiconductor sensors 21 to 2*n* can be removed by a capacitor 114 and a value proportional to the average number of photons in X-rays can be obtained accurately by integration in an integrator even in the case where a small number of incident photons are given. Furthermore, because the output signals just after X-ray irradiation are held by the sample/hold circuits 51 to 5*n* respectively, correction of the output signals as described above in the embodiment 1 is not required. Hence, the correction coefficient memory 16 is not required. Alternatively, the sample/hold circuits 51 to 5*n* may be provided on the first-stage circuits 111 to 11*n*.

(Embodiment 3)

Figure 6:
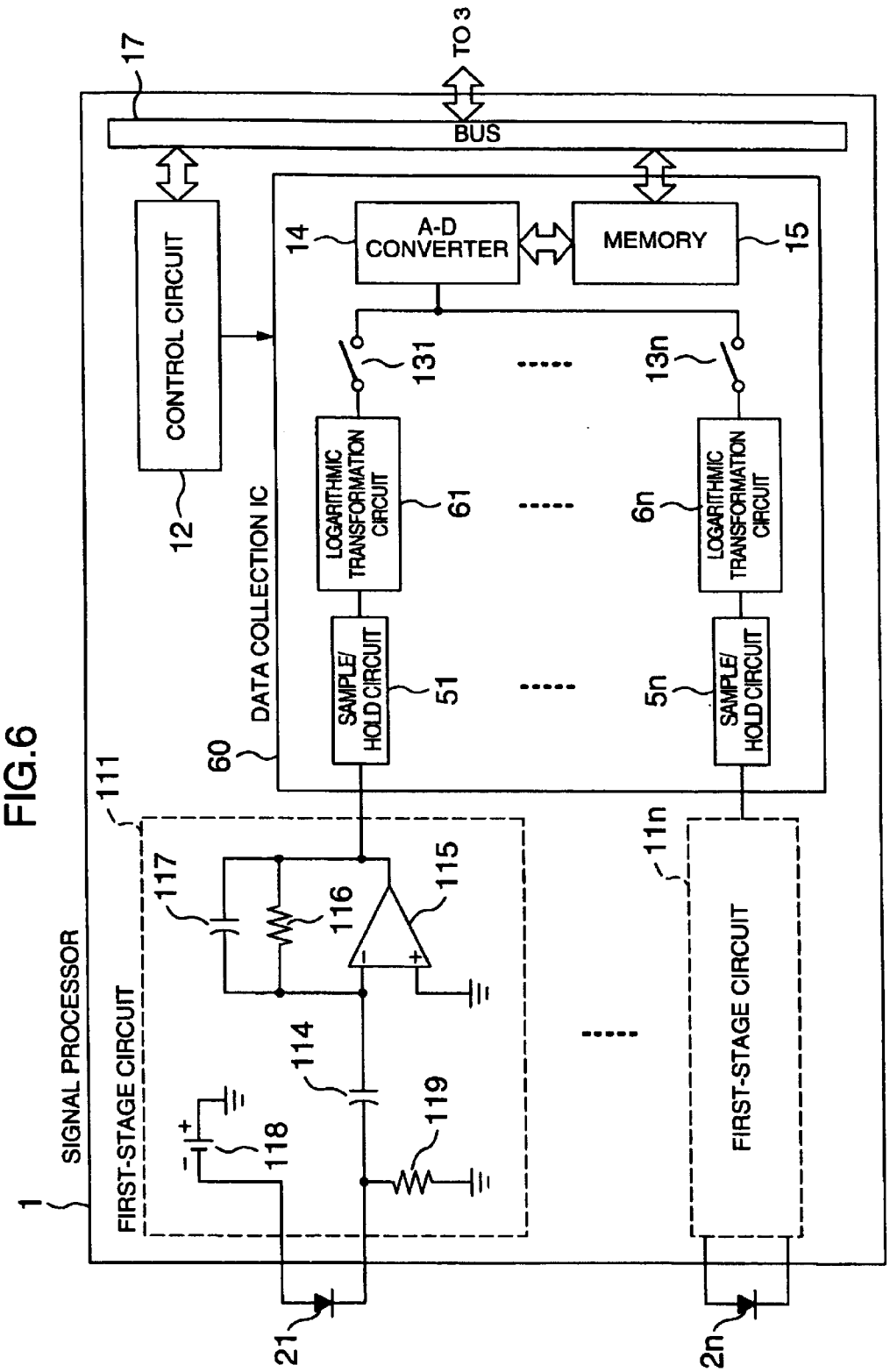
FIG. 6 shows a configuration diagram of a signal processor as a further embodiment of the present invention.

Referring to FIG. 6, a signal processor as a further embodiment of the present invention will be described below. This embodiment is different from the embodiment 2 in that logarithmic transformation circuits are added to the data collection IC. The point of difference from the embodiment 2 will be described below.

In the data collection IC 60, the output signals held by the sample/hold circuits 51 to 5*n* are supplied to the logarithmic transformation circuits 61 to 6*n* respectively. Upon reception of the output signals, the logarithmic transformation circuits 61 to 6*n* transform the output signals into logarithmic values and output the logarithmic values respectively. In the CT controller 9, the data required in calculation for reconstructing a perspective image are logarithmic-value data. Hence, because logarithmic transformation is performed in the signal processor 1 in advance, logarithmic transformation needs not to be performed in the CT controller 9. Calculation in the CT controller 9 can be simplified. Although this embodiment has shown the case where the logarithmic transformation circuits 61 to 6*n* are provided for performing logarithmic transformation, such calculation may be made by a software means in the control circuit 12 before data transmission.

(Embodiment 4)

Figure 7:
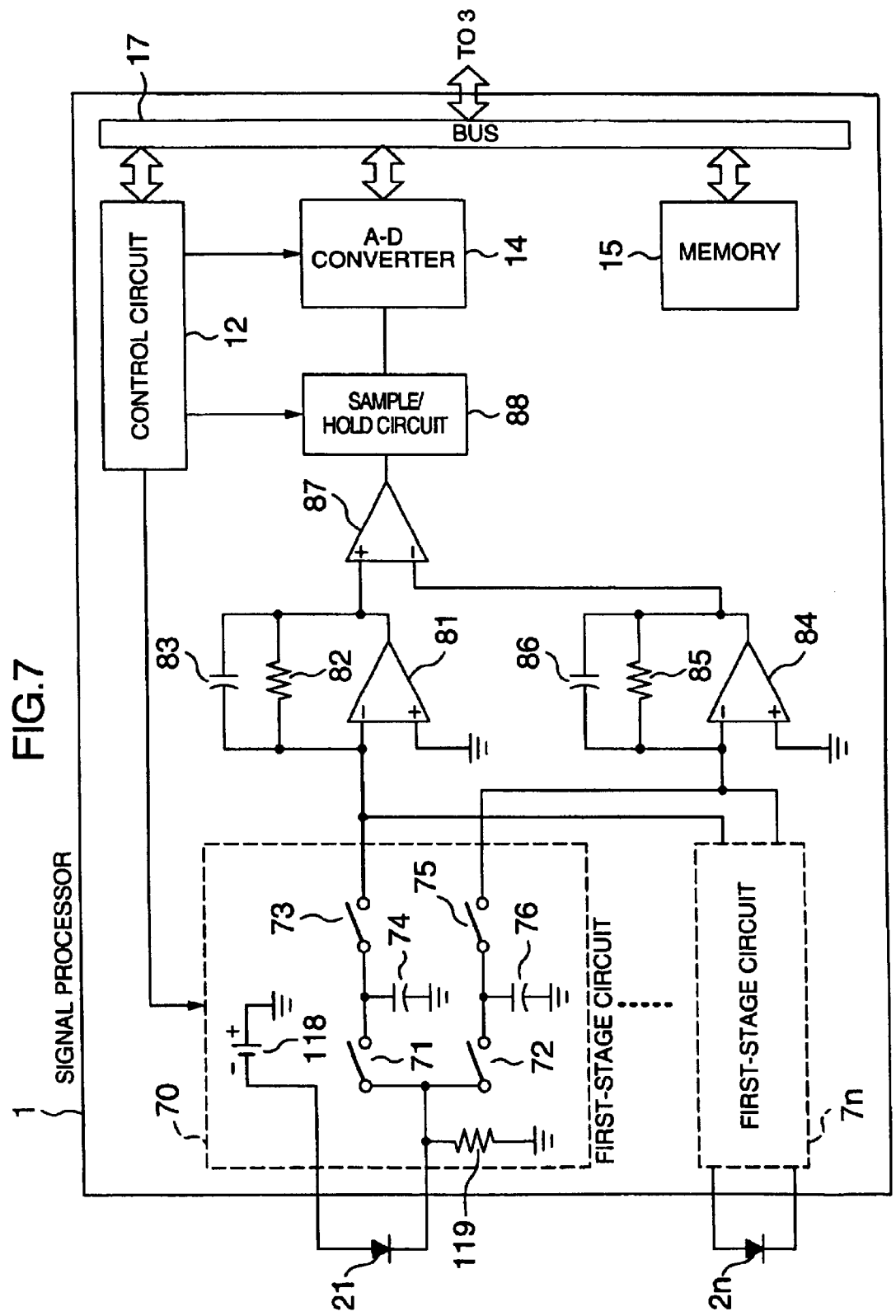
FIG. 7 shows a configuration diagram of a signal processor as a further embodiment of the present invention.

Referring to FIG. 7, a signal processor as a further embodiment of the present invention will be described below. Incidentally, the point of difference of this embodiment from the embodiment 1 will be mainly described below.

In a first-stage circuit 70 in FIG. 7, switches 71 and 72 are connected to a junction between the semiconductor sensor 21 and the resistor 119 so as to be parallel with each other. A switch 73 is further connected to the other end of the switch 71. A capacitor 74 is connected to a junction between the switches 71 and 73 while the other end of the capacitor 74 is connected to the ground. On the other hand, a switch 75 is further connected to the other end of the switch 72. A capacitor 76 is connected to a junction between the switches 72 and 75 while the other end of the capacitor 76 is connected to the ground.

The operation of the first-stage circuit 70 will be described. Before X-ray pulse irradiation starts, the switches 71 and 72 are closed and the switches 73 and 75 are opened. At the same time when X-ray pulse irradiation starts, the switch 71 is opened. On the other hand, the switch 72 is kept close during the X-ray pulse irradiation and the switches 73 and 75 are kept open during the X-ray pulse irradiation. Because the switch 72 is kept close during the X-ray pulse irradiation, electric charges due to a current, inclusive of a dark current, generated in the semiconductor sensor 21 by incidence of X-rays are stored (integrated) in the capacitor 76. Because the switch 71 is closed after the completion of the X-ray pulse irradiation, electric charges due to the dark current are stored (integrated) in the capacitor 74. Incidentally, in this embodiment, the resistance of the resistor 119 is set to be as large as 1 [MΩ] and the capacitance of the capacitors 74 and 76 is set to be equal to the capacitance 100 [pF] of the semiconductor sensor 21. As a result, the current generated by the X-ray pulse is prevented from flowing into the resistor 119 so that the current is made to flow into the semiconductor sensor 21 and the capacitor 76 equally.

Then, the switches 73 and 75 are closed, so that currents corresponding to the electric charges stored in the capacitors 74 and 76 flow into posterior circuits through the switches 73 and 75 respectively. An amplifier unit constituted by a combination of an operational amplifier 81, a resistor 82 and a capacitor 83 is connected to the switch 73. An amplifier unit constituted by a combination of an operational amplifier 84, a resistor 85 and a capacitor 86 is connected to the switch 75. The two amplifier units amplify input signals by the same amplification factors respectively and supply the amplified signals to a subtractor 87. Upon reception of the output signals of the two amplifier units, the subtractor 87 subtracts one signal from the other and supplies a result of the subtraction to an sample/hold circuit 88. That is, the subtractor 87 calculates the difference between a voltage corresponding to a current, inclusive of a dark current, generated in the semiconductor sensor 21 by incidence of X-rays and a voltage corresponding to the dark current. Hence, the output of the subtractor 87 is provided as a voltage corresponding to the current generated in the semiconductor sensor 21 by incidence of X-rays. Upon reception of the output signal of the subtractor 87, the sample/hold circuit 88 holds the signal and supplies the signal to the A-D converter 14. Upon reception of the output signal of the sample/hold circuit 88, the A-D converter 14 A-D converts the signal.

According to this embodiment, a voltage corresponding to a current generated by incidence of X-rays can be calculated accurately because the subtractor 87 calculates the difference between a voltage corresponding to a current inclusive of a dark current generated in each of the semiconductor sensors 21 to 2n by incidence of X-rays and a voltage corresponding to the dark current so that the voltage corresponding to the dark current generated in each of the semiconductor sensors 21 to 2n is removed. This technique is effective regardless of the number of incident photones.

Incidentally, the switch 71, the capacitor 74, the switch 73 and the amplifier unit using the operational amplifier 81 can be omitted. In this case, a voltage corresponding to the dark current is measured without X-ray irradiation and stored in the memory 15 before the measurement of the object starts. When the stored voltage corresponding to the dark current is subtracted from the measured value at the time of the measurement of the object, a voltage corresponding to the current generated by incidence of X-rays can be calculated accurately.

(Embodiment 5)

Figure 11:
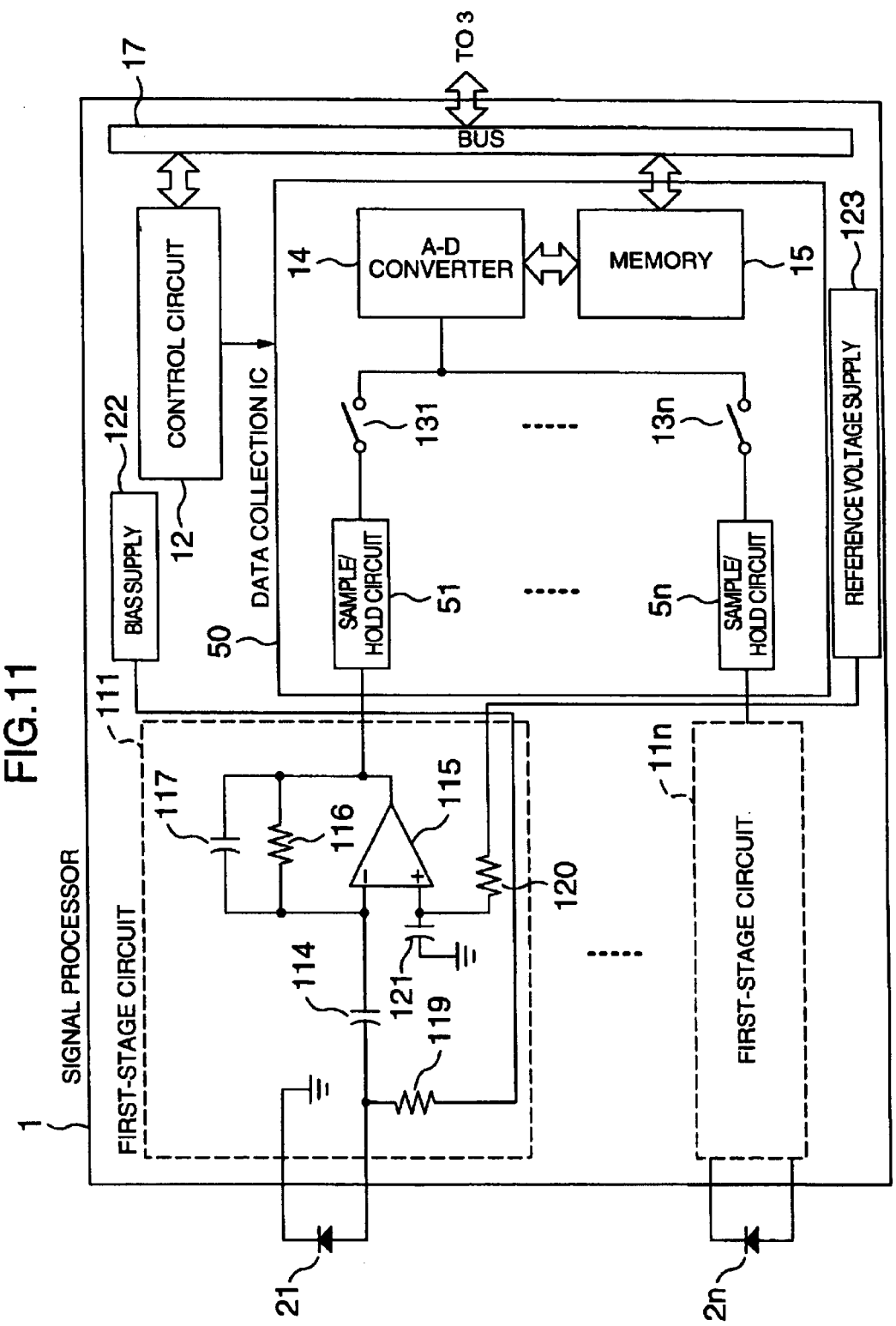
FIG. 11 is a configuration diagram of a signal processor as a further embodiment of the invention.

Referring to FIG. 11, a signal processor as a further embodiment of the invention will be described below. This embodiment is the same as Embodiment 2 in that a data collection IC in which sample/hold circuits and a multiplexer are incorporated in an A-D converter is used. This embodiment is, however, different from Embodiment 2 in the configuration of first-stage circuits. The point of difference from Embodiment 2 will be described below.

As shown in FIG. 11, a bias supply 122 and a reference voltage supply 123 are additionally provided in this embodiment as well as this embodiment is different from Embodiment 2 in the configuration of first-stage circuits 111 to 11n. In the first-stage circuit 111, first, a bias voltage is supplied to a semiconductor sensor 21 from a capacitor 114 through a resistor 119. Such a bias voltage is supplied to all the first-stage circuits 111 to 11n by the bias supply 122 additionally provided in the outside of the first-stage circuit 111. Also in this embodiment, the bias voltage is negative, so that semiconductor sensors in FIG. 11 are reverse to those in FIG. 5.

A positive-phase input side of an operational amplifier 115 is connected to the reference voltage supply 123 through a resistor 120. The reference voltage supply 123 supplies a voltage to all the first-stage circuits 111 to 11n. This is because the data collection IC used in this embodiment is of the bipolar type of ±2.5 V input. Hence, the reference voltage supply 123 always outputs 2.5 V, so that the operational amplifier 115 always outputs 2.5 V when X rays are not incident on the semiconductor sensor 21. When X-ray pulses are incident on the semiconductor sensor 21, the output of the operational amplifier 115 leans to one side. Accordingly, the measured value of the sensor output is obtained as 2.5 V—(the output voltage of the operational amplifier at the time of inputting of X-ray pulses). In such a configuration, full play can be given to the performance of the A-D converter 14 in the data collection IC even in the case where the A-D converter 14 is not unipolar but bipolar.

In this embodiment, values of other resistors and capacitors are set as follows. The value of each of resistors 119, 116 and 120 is 10 MΩ. The values of capacitors 117, 114 and 121 are 22 pF, 100 pF and 0.1 $\mu$F, respectively. Hence, the time constant of integration is 220 $\mu$s. Although the value of the capacitor 114 for AC coupling is generally often set to about 0.1 $\mu$F, it is set to a small value of 100 pF in this embodiment. In this case, the time constant of differentiation is 1 ms. When the time constant of differentiation is made small, the following advantage is obtained. In the case where the value of the capacitor 114 is set to 0.1 $\mu$F, the time constant of differentiation is 1 sec. In this case, error occurs in the output of the first-stage circuit 111 when intensive X-ray pulses are continuously input to the sensor (when, for example, X-rays are input to the sensor directly without passage through any object) though the X-ray pulses of an X-ray CT system are short pulses of 5 $\mu$s and small in low-frequency components. To reduce the error, the value of the capacitor 114 is set to 100 pF and the time constant of differentiation is set to 1 ms. That is, preferably, (the differential time constant of the first-stage circuit)<(the period Tp of the X-ray pulses).

As described above, in addition to the effect of Embodiment 2, this embodiment has an effect in which full play can be given to the performance of the A-D converter 14 in the data collection IC even in the case where the A-D converter 14 is bipolar and, accordingly, error can be prevented from occurring in the output of the first-stage circuit due to the DC component of the sensor current.

Incidentally, to prevent error from occurring in the output of the first-stage circuit due to the DC component of the sensor current, also in Embodiment 1 or 2, the value of the capacitor 114 may be determined in the same manner as described above. Further, a differential circuit may be additionally provided between the first-stage circuit 111 and the data collection IC 50.

(Embodiment 6)

Figure 12:
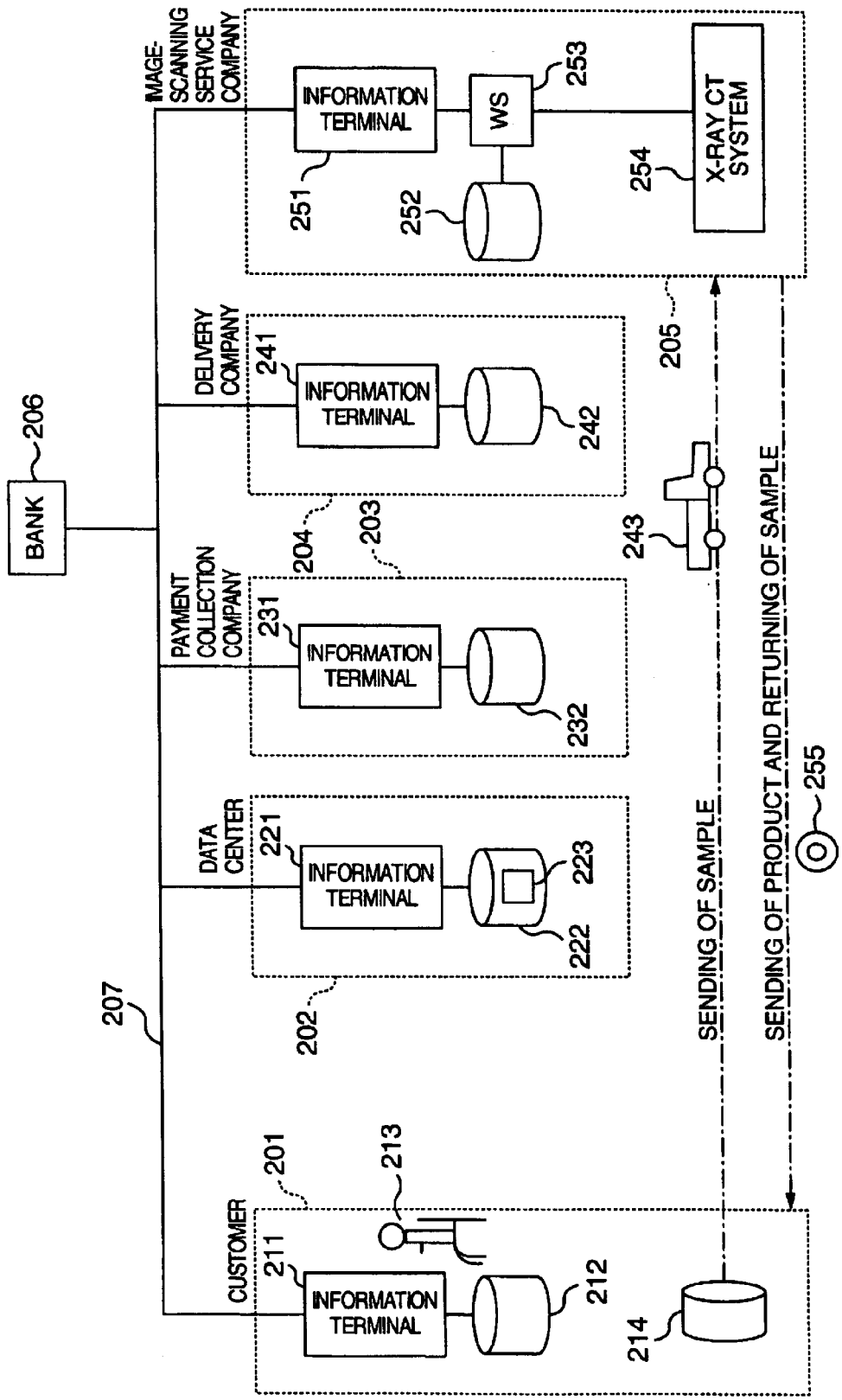
FIG. 12 is a schematic business system diagram of image scanning business as a further embodiment of the invention.

Next, an embodiment of image scanning business according to the invention will be described. FIG. 12 is a schematic business system diagram showing this embodiment. A customer 201 (generally, an enterprise), a data center 202, a payment collection company 203, a delivery company 204 and an image-scanning service company (CT scanning service company) 205 have information terminals 211, 221, 231, 241 and 251 respectively. Each of the information terminals 211, 221, 231, 241 and 251 is connected to a server in a bank 206 by a network 207. In this embodiment, the network is a private circuit. The network for connecting the information terminals may be a private circuit or may be an indirectly connecting network such as so-called Internet. Data storage devices 212, 222, 232, 242 and 252 are connected to the information terminals respectively. The information terminal 251 is further connected to a work station 253. The work station 253 controls an X-ray CT system 254, processes scanning image data, generates tomograms and stores the scanning image data. For example, a system shown in FIG. 2 is used as the X-ray CT system 254. An order management database 223 for management of image scanning ordering information is stored in the data storage device 222.

An employee 213, who is in the employ of the customer 201 and who desires to scan images, uses the information terminal 211 to make access to the data center 202 through the network 207. The employee 213 can extract information from the order management database 223 by making access to a home page stored in the order management database 223 of the data center 202. When the employee 213 inputs the kind of image data to be scanned, the delivery date thereof, etc., to the information terminal 211 so that information of a sample is input to the information terminal 221 and the order management database 223, the information terminal 221 examines whether the image data can be scanned or not and calculates an estimated amount. Thus, the employee 213 can find results of the examination and calculation from the data center 202.

When the customer 201 who has acquired these pieces of information inputs an ordering instruction to the order management database 223, the information of the order is sent to the respective information terminals of the payment collection company 203 and the image-scanning service company 205. The payment collection company 203 gives the customer 201 a credit, and the image-scanning service company 205 executes an order accepting process. Upon acceptance of the order, the image-scanning service company 205 requests the delivery company 204 to transport the sample. The delivery company 204 transports the sample 214 of the customer 201 to the image-scanning service company 205 by transportation means 243 (such as car, airplane, ship, etc., for example, by car in this embodiment). The image-scanning service company 205 scans images of the sample 214 by use of the X-ray CT system 254 on the basis of specifications which are registered in the order management database 223 in advance. After the completion of image scanning, the delivery company 204 requested by the image-scanning service company 205 to transport a product (recording medium containing scanning image data stored therein) 255 and the sample 214 delivers the product 255 and the sample 214 to the customer 201. Then, the image-scanning service company 205 informs the payment collection company 203 of the completion of image scanning, so that the payment collection company 203 charges the customer 201. When the customer 201 pays the charge through the bank 206, the bank 206 informs the payment collection company 203 of the completion of payment. Thus, an X-ray CT image scanning service is completed.

The flow of information in the X-ray CT image scanning service, the method of determining specifications of scanning image data, the content of scanning image data, the charge system and the configuration of the order management database 223 will be described below in detail.

Figure 13:
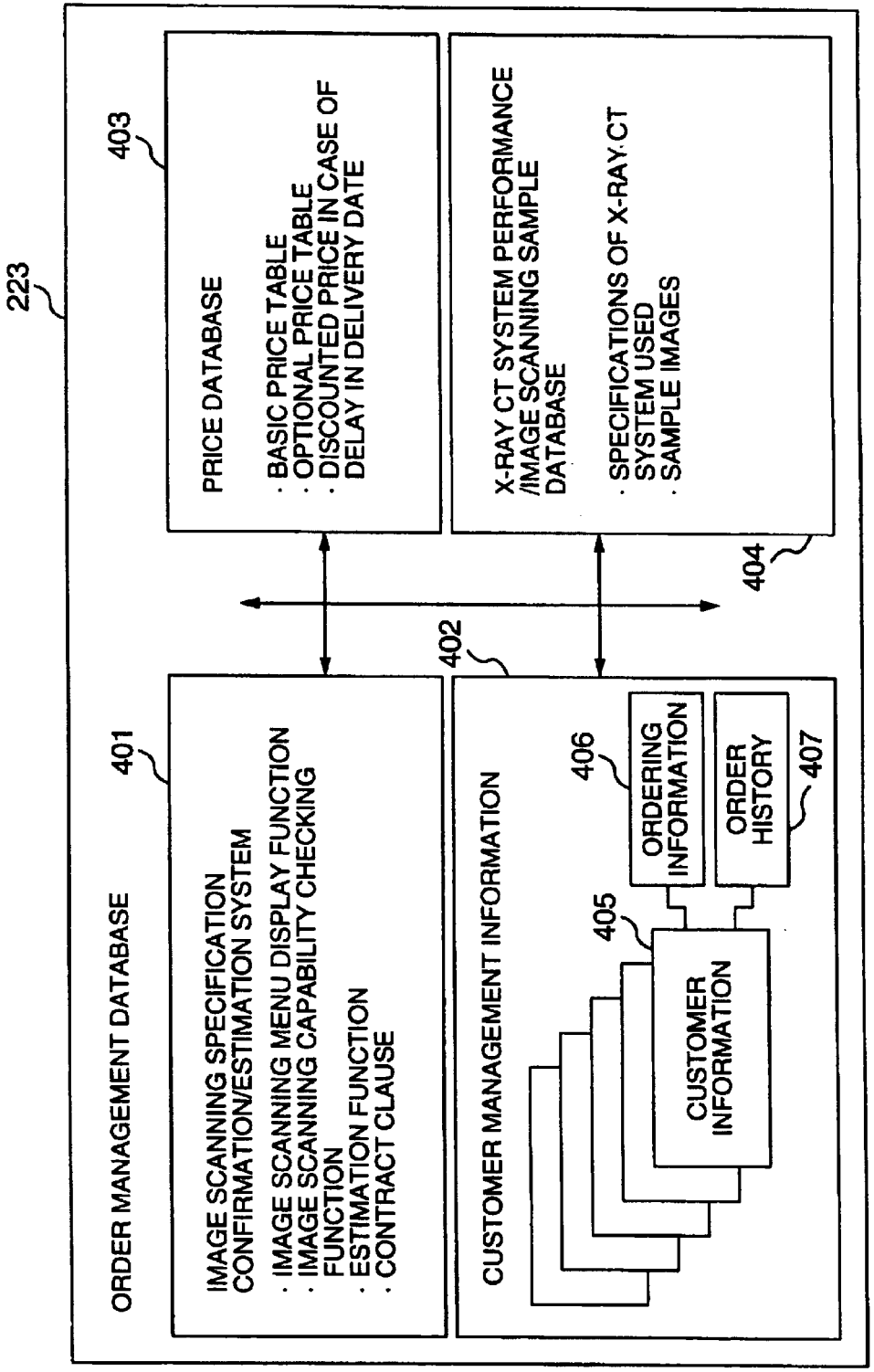
FIG. 13 is a configuration diagram of an order management database depicted in FIG. 12.

FIG. 13 shows the configuration of the order management database 223. The order management database 223 includes an image scanning specification confirmation/estimation system 401, a customer information management/ registration system 402, a price database 403, and an X-ray CT system performance/image scanning sample database 404. The order management database 223 is provided as a home page on the network. From the data center 202 or from the image-scanning service company 205, the content of the order management database 223 can be browsed through the information terminal network and, if necessary, the content of the order management database 223 can be amended. At that time, the browsing or amending operation is performed from the information terminal 221 or 251 through the network. From the payment collection company 203, the content of the order management database 223 can be browsed and required data can be written in the order management database 223. The customer 201 can perform registration of customer information, ordering procedures, confirmation of the content of the order, and so on.

The customer information management/registration system 402 stores customer information 405, and ordering information 406 and past order history information 407 both associated with the customer information 405. Information required for ordering an image scanning service, such as customer's name, company name, address, telephone number, payer's name, etc., is stored as the customer information 405. The image scanning specification confirmation/ estimation system 401 has an image scanning menu display function necessary for the customer to issue a request of scanning images, a check function for checking whether images can be scanned or not, an estimation function for estimating a price on the basis of the content of determined image scanning, and a contract display function for displaying a contract for the X-ray CT image scanning service. The price database 403 stores price data such as a basic price table for image scanning service, an optional price table, a discounted price in case of a delay in delivery date, and so on.

The X-ray CT system performance/image scanning sample database 404 is a database to make the customer know the content of image scanning service. The performance of the CT system used for scanning images and image samples of a subject scanned by the system are stored in the database 404. The price database 403 and the X-ray CT system performance/image scanning sample database 404 are databases for providing information to the customer when the customer uses the image scanning specification confirmation/estimation system 401 to request image scanning.

Figure 14:
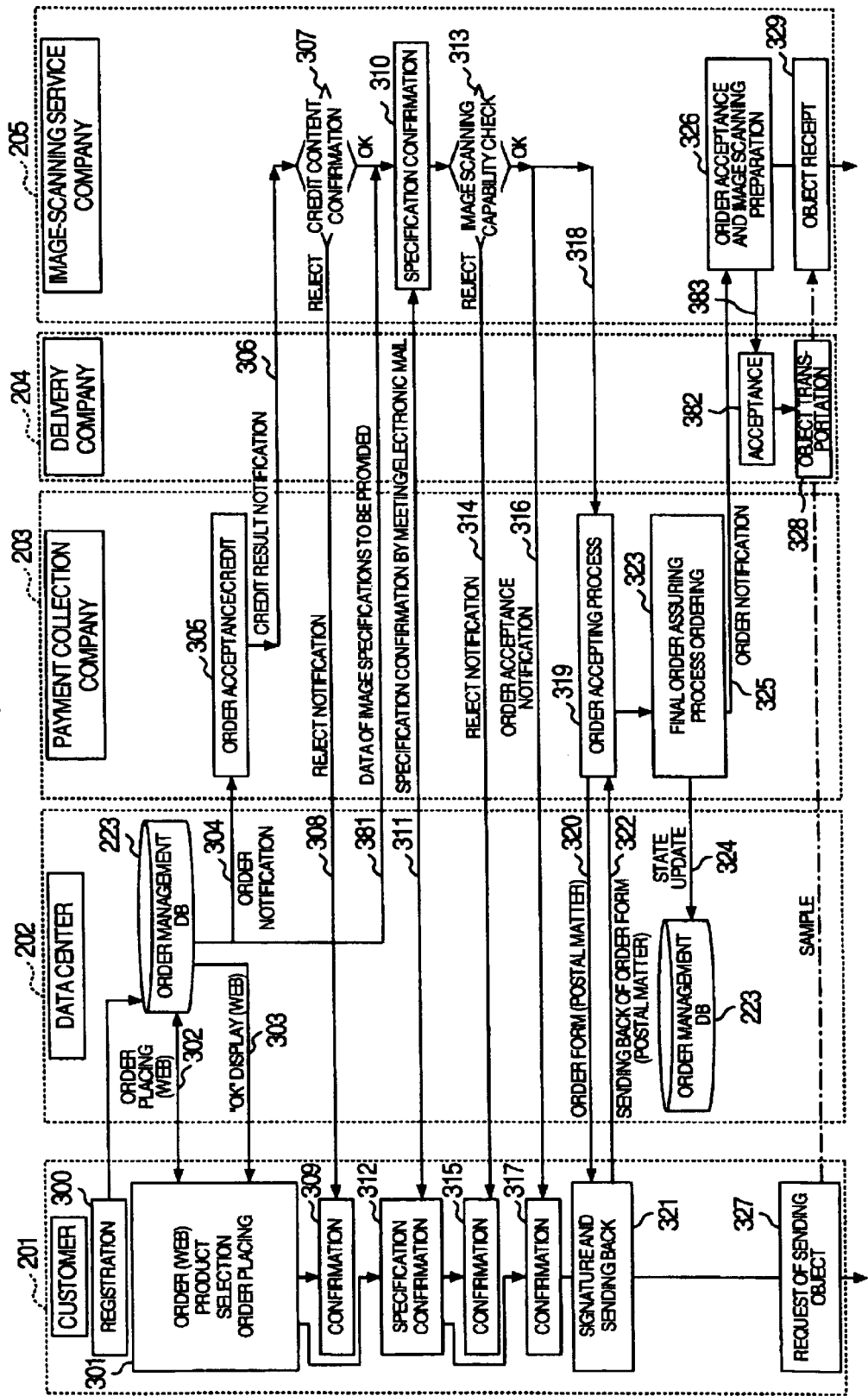
FIG. 14 is a diagram showing an example of an operation flow of image scanning business.

FIGS. 14 and 15 are diagrams showing flows of operations. Each of FIGS. 14 and 15 shows respective operations of the customer, the data center, the payment collection company, the delivery company and the image-scanning service company. Referring to FIGS. 14 and 15, order information, charge information, specifications of image scanning and a flow of sample and product will be described. Exchange of electronic mails and information among the customer 201, the data center 202, the payment collection company 203, the delivery company 204 and the image-scanning service company 205 is performed among corresponding information terminals through the network 207.

The customer 201 (in practice, the employee 213 (FIG. 12) belonging to the customer 201) first registers customer information into the order management database 223 through the information terminal 211 in order to place an order through the network. The customer 201 makes access to the order management database 223 in the data center 202 and inputs (300) customer information to the order management database 223 by operating the customer information management/registration system 402. As described above, information necessary for ordering image scanning service, such as customer's name, company name, address, telephone number, payer's name, etc., is registered as the customer information. When the customer information is registered, image scanning service (301) is allowed to be ordered.

The order is performed as follows. The customer 201 makes access to the image scanning specification confirmation/estimation system 401 of the order management database 223, makes an order processing screen exhibited on a display of the information terminal 211, and inputs required specifications of image scanning sequentially. The image scanning specification confirmation/estimation system 401 incorporated in the information terminal 221 checks whether images can be scanned or not and obtains an estimated price on the basis of the input specifications of image scanning and transmits (302) these pieces of information to the information terminal 211. When the registration of image scanning specification data is completed by the customer 201, the information terminal 221 sends "OK" display (303) back to the customer 201. When the "OK" display (303) is made, the information terminal 221 transmits (304) an order notification electronic mail to the information terminal 231 of the payment collection company 203. The order notification electronic mail 304 contains customer information.

Upon reception of the order notification electronic mail (304), the information terminal 231 of the payment collection company 203 checks credit (305) on the basis of the information. Credit check is executed by the information terminal or by an employee (not shown) working in the payment collection company. In this embodiment, credit check is executed by the information terminal. When checking of customer's credit is completed, the information terminal 231 of the payment collection company 203 transmits a credit result notification electronic mail (306) to the information terminal 251 of the image-scanning service company 205.

The image-scanning service company 205 confirms (307) the credit result notification electronic mail. When the content of the electronic mail is "NO" (reject), the information terminal 251 transmits a reject notification electronic mail (308) to the information terminal 211 of the customer 201. In this case, the ordering operation is terminated at the point of time when the customer 201 receives and confirms the reject notification electronic mail. When the confirmation of credit content 307 is "OK", the image-scanning service company 205 uses the information terminal 251 to acquire (381) image scanning specification data from the ordering information 406 (FIG. 13) input to the customer information management/registration system 402 of the order management database 223 and to confirm the ordered specifications. If there is some blank or ambitious portion in the ordered specifications, data transfer is performed between the customer 201 and the image-scanning service company 205 to assure the specifications (311).

The image-scanning service company 205 makes a final check on the basis of the final specification data as to whether images can be scanned or not (313). In the case of reject, the image-scanning service company 205 transmits a reject electronic mail (314) to the customer 201 through the information terminal 251. In the case of reject, the ordering operation is terminated at the point of time when the customer 201 receives the electronic mail 314. In the case where the check 313 as to whether the image can be scanned or not is "OK", the image-scanning service company 205 transmits an order acceptance electronic mail (316) to the customer 201 and, at the same time, transmits an order acceptance electronic mail 318 to the payment collection company 203. The order acceptance electronic mail contains information such as customer information, estimated specifications (image scanning contents), an estimated price and the delivery date.

Upon reception of the order acceptance electronic mail 318, the payment collection company 203 carries out an order acceptance process (319). In the order acceptance process (319), an order form 320 is created on the basis of the information stored in the order acceptance electronic mail 318. The order form contains the aforementioned information such as customer information, estimated specifications (image scanning contents), an estimated price and the delivery date and contract clauses displayed also in the image scanning specification confirmation/estimation system 401 of the order management database 223. When the order form is completed, the order form 320 is sent to the customer 201 as a postal matter.

When the customer 201 acquires the order form 320, the customer 201 confirms the content of the order form 320, signs (321) it and returns it as an approved order form 322 to the payment collection company 203. Although this embodiment has shown the case where the order form is a document sent as a postal matter, this order form may be processed on the network to achieve paperless management. Upon reception of the approved order form, the payment collection company 203 carries out a final order assuring process 323. In the final order assuring process 323, ordering information 406 (see FIG. 13) of corresponding customer information 405 from the customer information management/registration system 402 of the order management database 223 incorporated in the data center 202 is updated and assured to be the ordering content by the information terminal 231 (324). The payment collection company 203 sends an order notification electronic mail 325 also to the image-scanning service company 205.

The image-scanning service company 205 carries out an order acceptance/image scanning preparation process (326) on the basis of the order notification electronic mail 325 received from the payment collection company 203. That is, the image-scanning service company 205 transmits delivery request information 383 to the delivery company 204 and prepares for image scanning in the company. Upon reception of the delivery request information 383, the delivery company 204 accepts the information 383 (382), accepts the image scanning sample delivery request 327 from the customer 201 and transports the sample 255 (FIG. 12) received from the customer 201 to the image-scanning service company 205 by a truck 243. In this embodiment, the delivery fee for a round trip is charged to the customer 201. Hence, a flow of charges between the delivery company 204 and the customer 201 is not shown.

The image-scanning service company 205 receives the sample from the delivery company 204 (329) and starts an image scanning operation. FIG. 15 shows a flow of operations after the image scanning operation (330). The image-scanning service company 205 starts the image scanning operation 330 on the basis of the acceptance of the order. The delivery date data is input (332) to corresponding ordering information 406 in the data center 202 in accordance with the image scanning schedule of the image-scanning service company 205. When the delivery date is delayed, the delivery date can be corrected. The inputting of the ordering information 406 to the data center 202 and the correction of the delivery date can be performed by transmitting information from the information terminal 251 to the information terminal 221 and adding the information to the ordering information 406 in the database 223.

The customer 201 can confirm (333) the content and progress of the order by making access to the order management database 223 in the data center 202 from the information terminal 211 through the information terminal 221. With respect to the progress of the order, when the order number written in the order form is input (334), the ordering information 406 of the order management database 223 can be listed (335) on the display in the information terminal 211. The confirmation (337) of the delivery date by the customer 201 is performed by exchange of electronic mails (336) between the customer 201 and the customer contact window 340 of the image-scanning service company 205. Other technical inquiries (338) are made by exchange of electronic mails (339) between the customer 201 and the customer contact window 340 of the image-scanning service company 205.

When the image scanning operation is completed, the image-scanning service company 205 forwards the customer 201 a recording medium having scanning image data recorded therein as a product (341). Although this embodiment has shown the case where the product is a recording medium, the scanning image data may be sent to the information terminal of the customer through the network. The product and the sample received from the customer 201 in trust are delivered (342) to the customer 201 by the delivery company 204. When the customer 201 receives the product and the sample (345), the delivery company 204 transmits the confirmation information 347 of the delivery to the image-scanning service company 205. When the image-scanning service company 205 confirms the delivery (348), the image-scanning service company 205 transmits product delivery completion notification information 349 to the payment collection company 203.

Upon reception of the product delivery completion notification information 349, the payment collection company 203 makes delivery completion registration 350 and updates corresponding ordering information in the order management database 223. In practice, the product delivery completion information is added to ordering information 406 of corresponding customer information 405 in the customer information management/registration system 402 in the order management database 223. As a result, the order management database 223 transfers a confirmation electronic mail to the image-scanning service company 205.

After the delivery completion registration 350, the payment collection company 203 further issues a bill and bank account slip 354 and sends it to the customer 201. At this point of time, the customer 201 has received the product (345) and inspected it (346). Hence, after the customer 201 receives the bill and bank account slip 354, the customer 354 pays the charge in the designated account 261 (356). The designated account 261 is an account of the payment collection company 203 but is managed by the bank 206 (FIG. 12). The charge paid in the designated account 261 is settled to be finally sent to the image-scanning service company 205 (358).

Further, paying-in information 357 from the bank 206 is transmitted to the payment collection company 203. Upon confirmation of the payment (359), the payment collection company 203 sends payment confirmation information 360 to the order management database 223 in the data center 202. As a result, the order management database 223 of the data center 202 transmits a completion electronic mail 370 to the image-scanning service company 205. When the completion electronic mail 370 is received by the image-scanning service company 205, the image scanning service is completed.

When the promised delivery date is delayed, an amount of money discounted from the contracted price may be requested. Because the delivery date data is input to the order management database in the image-scanning service company (332), the payment collection company 203 carries out a process of discounting the charged amount on the basis of the delivery date data when the bill is sent. In this embodiment, generally, the standard period of delivery is set to one week from the point of time when the sample is delivered to the image-scanning service company to the point of time when the image scanning operation is completed. Accordingly, the discounting process may be made so that the estimated charge is discounted by 20% for every one week delay after the promised delivery date.

Although this embodiment has shown the case where the order forms 320 and 322 and the bill and bank account slip 354 are all sent as postal matters, this is aimed at attaining matching with the conventional business model and all or part of exchange of these pieces of information may be executed on the network.

Referring to FIG. 16, the actual content of the X-ray CT image scanning service will be described below. FIG. 16 shows a menu 400 of image scanning service carried out in this embodiment. The service menu 400 is stored in the image scanning specification confirmation/estimation system 401 in the order management database 223. When the customer 201 places an order, the customer 201 can browse the service menu 400 by using the information terminal 211.

The basic service is roughly classified into two categories: specific section photography and stereoscopic image photography. Each of the two categories has basic service and optional service. Common option is further provided.

Information obtained by the specific section photography is displayed by 2D sections. As basic data, 2D bit-map data (containing density information in each pixel) obtained by CT image scanning and 2D image data transformed so that the 2D bit-map data can be viewed on a screen of a general-purpose personal computer are provided to the customer. Further, as optional service, measurement of dimensions in a region designated by the customer is provided, that is, for example, distance data between two points and display data of density distribution in a designated line/region are provided.

Information obtained by the stereoscopic image photography is displayed by a 3D stereoscopic image. As basic data, 3D bit-map data and a display software program for viewing the 3D bit-map data are collectively provided to the customer. As optional service, volume rendering data to make it possible to display the 3D bit-map data as a stereoscopic image, slicing display data to make it possible to view an image sliced at a designated portion, surface display data for displaying a surface of the sample, data of dimensions measured in a 3D designated position and density distribution display data in a designated line/region are provided.

Further, as common option, perspective image data similar to X-ray transparent photographs and standard sample photographing data for confirming the performance of the X-ray CT system used can be provided. The product provided to the customer is a combination of a report and a recording medium. The customer inspects and receives the product by confirming the report and unsealing the sealed recording medium.

As described above, in accordance with this embodiment, there can be constructed an X-ray CT image scanning system in which the customer can perform determination and ordering of specifications of images of a sample to be scanned efficiently and can acquire desired scanning image data efficiently. An image scanning condition determined on the basis of the performance of the X-ray CT system possessed by the X-ray CT image scanning system and the specifications of the sample can be demonstrated clearly to the customer. Accordingly, there can be provided a system in which the judgment as to whether images can be scanned or not and the content of image scanning can be determined automatically. Accordingly, image scanning service can be provided speedily and inexpensively compared with the case where a sales staff accepts an order of CT image scanning service. In this manner, in accordance with this embodiment, there can be provided a CT image scanning service in which X-ray CT images requested by the customer can be delivered to the customer in a shorter time.

Although this embodiment has shown the case where a data center is established separately from the image-scanning service company, the image-scanning service company may serve also as the data center. In this case, the cost for maintaining the data center can be reduced.

Although the aforementioned embodiments have shown the case where capacitors are used for removing dark currents, the invention may be applied also to the case where the capacitors are replaced by filters so long as the filters can remove DC components. Although the aforementioned embodiments have shown the case where semiconductor sensors are used as X-ray sensors because X-ray CT systems using high-energy X-ray pulses are provided as subjects of the embodiments, the invention may be applied also to the case where photodiodes, or the like, for measuring scintillator light or fluorescence are used as the sensors. In addition, the signal processors in the embodiments may be applied to other systems than the X-ray CT systems so long as the systems can emit pulse-like X-rays and measure the X-rays.

What is claimed is:

1. An X-ray CT apparatus comprising:

X-ray irradiation means for irradiating an X-ray to an object to be inspected;

an X-ray semiconductor sensor for detecting an X-ray passed through the object to be inspected and providing an output signal indicative thereof;

an X-ray sensor signal processing circuit for processing the output signal from the X-ray semiconductor sensor; and a CT control apparatus for reconstructing an image of the object to be inspected on the basis of the output signal of the X-ray semiconductor sensor processed by the X-ray sensor signal processing circuit;

wherein the X-ray sensor signal processing circuit comprises a filter for removing a DC component from the output signal of the X-ray semiconductor sensor and an integration circuit for integrating the output signal of the X-ray semiconductor sensor from which the DC component is removed by the filter.

2. The X-ray CT apparatus according to claim 1, further comprising a hold circuit for holding an output signal of the integration circuit.

3. The X-ray CT apparatus according to claim 1, further comprising a hold circuit for holding an output signal of the integration circuit, and a logarithmic conversion circuit for converting the output signal of the integration circuit held by the holding circuit to a logarithmic value.

4. The X-ray CT apparatus according to claim 1, further comprising a hold circuit for holding an output signal of the integration circuit, and correcting means for correcting the output signal of the integration circuit held by said holding circuit with a correction coefficient previously determined on the basis of an elapsed time after irradiation of the X-ray and a time constant of the integration circuit.

5. An X-ray CT apparatus comprising:

X-ray irradiation means for irradiating an X-ray to an object to be inspected;

an X-ray semiconductor sensor for detecting an X-ray passed through the object to be inspected and providing an output signal indicative thereof;

an X-ray sensor signal processing circuit for processing the output signal from the X-ray semiconductor sensor; and a CT control apparatus for reconstructing an image of the object to be inspected on the basis of the output signal of the X-ray semiconductor sensor processed by the X-ray sensor signal processing circuit;

wherein the X-ray sensor signal processing circuit comprises a filter for removing a DC component from the output signal of the X-ray semiconductor sensor and an integration circuit for integrating the output signal of the X-ray semiconductor sensor from which the DC component is removed by the filter; and wherein the integration circuit outputs an output signal on the basis of a time constant which is set so that the output signal of the integration circuit becomes zero after irradiation of the X-ray from the X-ray irradiation means until a next irradiation of an X-ray.

6. An X-ray CT apparatus comprising:

X-ray irradiation means for irradiating an X-ray pulse to an object to be inspected;

an X-ray semiconductor sensor for detecting an X-ray passed through the object to be inspected and providing an output indicative thereof;

an X-ray sensor signal processing circuit for processing the output signal of said X-ray semiconductor sensor; and a CT control apparatus for reconstructing an image of the object to be inspected on the basis of the output signal of the X-ray semiconductor sensor processed by the X-ray sensor signal processing circuit;

wherein the X-ray sensor signal processing circuit comprises a filter for removing a DC component from the output signal of the X-ray semiconductor sensor and an integration circuit for integrating the output signal of the X-ray semiconductor sensor from which the DC component is removed by the filter in order to obtain a voltage proportional to a number of photons of an incident X-ray pulse, an AD converter for executing AD conversion for an output signal of said integration circuit, and correcting means for correcting the output signal of the integration circuit AD converted by the AD converter on the basis of a time after the output signal is output from the integration circuit until the AD conversion is executed by the AD converter and a time constant of the integration circuit.

* * * * *